(12) United States Patent
Lunn et al.

(10) Patent No.: US 7,557,121 B2
(45) Date of Patent: *Jul. 7, 2009

(54) TETRAHYDRONAPHTHYRIDINE DERIVATIVES

(75) Inventors: Graham Lunn, Canterbury (GB); John Paul Mathias, Ashford (GB); Ross Sinclair Strang, Ramsgate (GB)

(73) Assignee: Pfizer Inc, New York, NY (US)

( * ) Notice: Subject to any disclaimer, the term of this patent is extended or adjusted under 35 U.S.C. 154(b) by 137 days.

This patent is subject to a terminal disclaimer.

(21) Appl. No.: 11/128,804

(22) Filed: May 12, 2005

(65) Prior Publication Data

US 2005/0256135 A1 Nov. 17, 2005

Related U.S. Application Data

(60) Provisional application No. 60/585,139, filed on Jul. 1, 2004.

(30) Foreign Application Priority Data

May 12, 2004 (EP) .................................. 04291222

(51) Int. Cl.
A61K 31/44 (2006.01)
C07D 515/02 (2006.01)

(52) U.S. Cl. ...................................... 514/300; 546/122
(58) Field of Classification Search ................. 546/122; 514/300
See application file for complete search history.

(56) References Cited

U.S. PATENT DOCUMENTS

| 6,878,736 B1 | 4/2005 | Kalindjian et al. | 514/408 |
| 2006/0173012 A1 | 8/2006 | Hohlweg | 514/252.02 |
| 2007/0179175 A1* | 8/2007 | Lunn | 514/300 |

FOREIGN PATENT DOCUMENTS

| EP | 1295883 | 3/2003 |
| RU | 2182904 | 10/2007 |
| WO | WO 9111172 | 8/1991 |
| WO | WO 9402518 | 2/1994 |
| WO | WO 9855148 | 12/1998 |
| WO | WO 0006254 | 2/2000 |
| WO | WO 0035298 | 6/2000 |
| WO | WO 0206223 | 1/2002 |
| WO | WO 0212190 | 2/2002 |
| WO | WO 0212214 | 2/2002 |
| WO | WO 02076925 | 10/2002 |
| WO | 03/076427 | * 9/2003 |

OTHER PUBLICATIONS

Boie et al., European Journal of Pharmacology, vol. 380,1999, pp. 203-213.*
Pokorny et al., Journal of Organic Chemistry (1972), 37(20), pp. 3101-5.*
Wijtmans et al., Expert Opin. Investg. Drugs, 2007, vol. 16 pp. 967-985.*
Haleblian, J. Pharm. Sci., 64(8), pp. 1269-1288 (1975).
J. Amer. Chem. Soc. 110(12), pp. 3965-3969 (1988).
L. Estel et al., J. Org. Chem. 53(12), pp. 2740-2744 (1988).
T. Sakamoto et al., Chem. And Pharm. Bull. 33(11), pp. 4764-4768 (1985).
Liang and Chen, Expert Opinion in Therapeutic Patents, 11(6), pp. 981-986 (2001).
Verma et al., Pharm. Technology On-line, 25(2), pp. 1-14 (2001).
Finnin and Morgan, J. Pharm. Sci. 88(10), pp. 955-958 (1999).
H. Stark, Expert Opinion Ther. Patents, vol. 13, No. 6, pp. 851-865, 2003.
US 2006/0173012 is English equivalent to RU 2006101452.
US 6,878,736 is English equivalent to RU 2214406.
Snyman et al., Immunopharmacology, 30(1), pp. 71-78, 1995.
Varty et al., Eur J. Pharmacol, 452(3), pp. 339-45, 2002.

* cited by examiner

Primary Examiner—D. Margaret Seaman
Assistant Examiner—Niloofar Rahmani
(74) Attorney, Agent, or Firm—Gregg C. Benson; Robert T. Ronau

(57) ABSTRACT

The present invention relates to tetrahydronaphthyridine derivatives of the general formula (I):

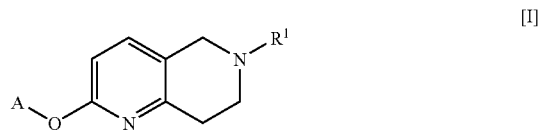

or of the general formula (I')

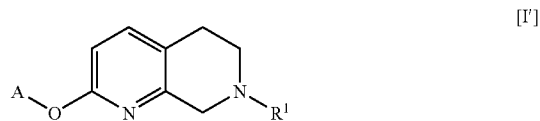

in which A and $R^1$ are as defined within, and to processes for the preparation of, intermediates used in the preparation of, compositions containing and the uses of, including the treatment diseases mediated by H3 ligands, in particular inflammatory, allergic and respiratory diseases, disorders and conditions.

14 Claims, No Drawings

TETRAHYDRONAPHTHYRIDINE DERIVATIVES

CROSS-REFERENCE TO RELATED APPLICATION

This patent application claims the benefit of U.S. Provisional Application Ser. No. 60/585,139, filed on Jul. 1, 2004 and European Patent Application No. 04291222.0, filed on May 12, 2004, both of which are herein incorporated by reference in their entirety.

FIELD OF THE INVENTION

The present invention relates to tetrahydronaphthyridine derivatives of the general formula (I):

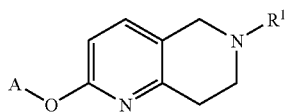

[I]

or of the general formula (I')

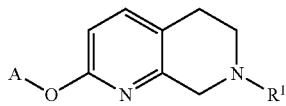

[I']

in which A and $R^1$ are as defined below, and to processes for the preparation of, intermediates used in the preparation of, compositions containing and the uses of, such derivatives.

BACKGROUND OF THE INVENTION

Histamine $H_3$ receptors are found inter alia on presynaptic terminals of peripheral nerves, where they modulate autonomic neurotransmission and modulate a variety of end organ responses under control of the autonomic nervous system. They are also heteroreceptors, modulating the release of numerous other neurotransmitters such as dopamine, glutamate, noradrenaline, serotonin, GABA, acetylcholine, some peptides and co-transmitters.

Recently numerous histamine $H_3$ receptor ligands have been developed. An overview of the current advance in $H_3$ ligand research and patenting is given in *Expert Opin. Ther. Patents* (2003) 13(6). Examples of Histamine $H_3$ receptor ligands can be found in WO02/76925, WO00/06254, WO02/12190, WO02/12214 and WO02/06223.

$H_3$ receptor ligands are believed to be suitable for the treatment of various diseases including both disorders of the central nervous system and inflammatory disorders. Examples of diseases where treatment with $H_3$ ligands is believed to be useful are inflammatory bowel disease, Crohn's disease, colitis ulcerosa, sleep disorders, migraine, dyskinesia, stress-induced anxiety, psychotic disorders, epilepsy, Cognition deficiency diseases such as Alzheimer's disease or mild cognitive impairment, depression, mood disorders, schizophrenia, anxiety disorders, attention-deficit hyperactivity disorder (ADHD), psychotic disorders, obesity, dizziness, epilepsy, motion sickness, vertigo, female and male sexual dysfunction, respiratory diseases such as adult respiratory distress syndrome, acute respiratory distress syndrome, bronchitis, chronic bronchitis, chronic obstructive pulmonary disease, cystic fibrosis, asthma, emphysema, rhinitis, chronic sinusitis, allergy, allergy-induced airway responses, allergic rhinitis, viral rhinitis, non-allergic rhinitis, perennial and seasonal rhinitis, nasal congestion, allergic congestion.

Although $H_3$ ligands are known there is still a need to provide new $H_3$ ligands that are good drug candidates. In particular, preferred compounds should bind potently to the histamine $H_3$ receptor whilst showing little affinity for other receptors. They should be well absorbed from the gastrointestinal tract, be metabolically stable and possess favourable pharmacokinetic properties. They should be non-toxic and demonstrate few side-effects.

SUMMARY OF THE INVENTION

The present invention provides a compound of formula (I):

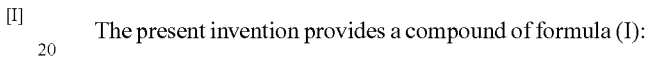

[I]

or of formula (I')

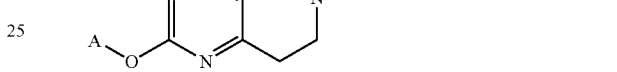

[I']

a stereoisomer thereof, or a pharmaceutically acceptable salt of said compound or stereoisomer, wherein:

$R^1$ is $het^1$, optionally substituted by one or two substituents independently selected from:
halogen
$(C_1-C_4)$alkyl, optionally substituted by halogen
$(C_1-C_4)$alkoxy, optionally substituted by halogen
—CN
morpholino
—$NR^2R^3$
—$(CH_2)_nC(O)NR^2R^3$
—$(CH_2)_nC(O)O$—$R^4$
—$(CH_2)_n$—$NR^5$—$C(O)$—$R^4$
—$(CH_2)_n$—$NR^5$—$C(O)$—$NR^2R^3$
—$SO_2$—$NR^2R^3$
—$SO_2$—$(C_1-C_4$ alkyl)
—$R^6$
—O—$R^6$ wherein independently for each substituent:
n is an integer selected from 0, 1, 2 and 3
$R^2$ $R^3$, are independently from each other selected from hydrogen and $(C_1-C_4)$alkyl or $R^2$ and $R^3$ taken together with the N atom to which they are attached form a 4, 5, 6 or 7 membered saturated heterocycle
$R^4$ and $R^5$ are independently from each other selected from hydrogen and $(C_1-C_4)$alkyl R[6] is phenyl, optionally substituted by halogen, ($C_1$-$C_4$)alkyl or ($C_1$-$C_4$)alkoxy A is:

(i) a group of formula:

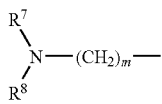

wherein
m is an integer from 2 to 6
R[7] and R[8] are each independently selected from hydrogen, ($C_1$-$C_6$)alkyl, ($C_3$-$C_7$)cycloalkyl and hydroxy($C_1$-$C_6$ alkyl) or
R[7] and R[8] taken together with the N atom to which they are attached form a 4-, 5-, 6- or 7-membered saturated heterocycle, wherein one C atom is optionally replaced by N, O, S, SO or $SO_2$ and wherein said saturated heterocycle is optionally substituted by one or two groups independently selected from ($C_1$-$C_4$)alkyl, ($C_1$-$C_4$)alkoxy, ($C_1$-$C_4$)alkoxy($C_1$-$C_4$)alkyl, hydroxy($C_1$-$C_4$)alkyl, hydroxy, C(O)O($C_1$-$C_4$)alkyl, —C(O)—($C_1$-$C_4$)alkyl-$NH_2$, —C(O)$NH_2$, halo, amino, ($C_1$-$C_4$)alkylamino and di[($C_1$-$C_4$)alkyl]amino or (ii) a group of formula:

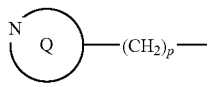

wherein
p is an integer selected from 0, 1 and 2
Q represents a 4, 5 or 6 membered saturated heterocycle optionally substituted by hydrogen, ($C_1$-$C_6$)alkyl, ($C_3$-$C_7$)cycloalkyl, hydroxy($C_1$-$C_6$)alkyl, —($C_1$-$C_4$)alkyl-COOH and —($C_1$-$C_4$)alkyl-O—($C_1$-$C_4$)alkyl-COOH wherein het[1] is selected from monocyclic or bicyclic heteroaromatic groups having 5 to 10 ring members, which contain 1, 2, 3 or 4 heteroatom(s) selected from nitrogen, oxygen and sulphur.

DETAILED DESCRIPTION

The advantage of the compounds of the invention is that they combine an increased $H_3$ potency with a potential for reduced cardiovascular side effects. Assays for determining $H_3$ potency and cardiovascular side effects are given in the experimental section hereafter ($H_3$ cell based functional assay and dofetilide binding to the hERG product, respectively).

In the present description the following definitions are used, unless otherwise specified: "halo" denotes a halogen atom selected from the group consisting of fluoro, chloro, bromo and iodo. "($C_1$-$C_x$)alkyl" denotes a saturated, straight-chain or branched hydrocarbon group having from 1 to x carbon atoms and includes for example (when x=4) methyl, ethyl, propyl, i-propyl, n-butyl, i-butyl, sec-butyl and t-butyl and further (when x=6) pentyl, 1-pentyl, n-pentyl and hexyl. This also applies if they carry substituents or occur as substituents of other radicals, for example in ($C_1$-$C_4$)alkoxy radicals, hydroxy($C_1$-$C_6$)alkyl radicals, ($C_1$-$C_4$)alkoxy($C_1$-$C_4$)alkyl radicals, ($C_1$-$C_4$)alkylamino radicals, di[($C_1$-$C_4$)alkyl]amino radicals, ($C_1$-$C_4$)alkyl-COOH radicals, ($C_1$-$C_4$)alkyl-O—($C_1$-$C_4$)alkyl-COOH radicals etc. . . . Examples of suitable ($C_1$-$C_4$)alkoxy radicals are methoxy, ethoxy, n-propoxy, iso-propoxy, n-butoxy, iso-butoxy, sec-butoxy and tert-butoxy. hydroxy($C_1$-$C_4$)alkyl radicals are alkyl radicals substituted by hydroxy. They can contain 1 or several hydroxy substituents, if not stated otherwise. Examples of suitable hydroxy($C_1$-$C_6$)alkyl radicals are hydroxymethyl, 1-hydroxyethyl or 2-hydroxyethyl.

In the case where the ($C_1$-$C_x$)alkyl radicals are substituted by halo, such radical can contain 1 or several halogen atoms, if not stated otherwise. Said halo is preferably a fluoro, a chloro, a bromo or a iodo, in particular fluoro or chloro. For example in a fluoro-substituted alkyl radical, a methyl group can be present as a difluoromethyl or a trifluoromethyl group.

"($C_3$-$C_7$)cycloalkyl" denotes a saturated monocyclic carbocyclic group having 3 to 7 carbon atoms and includes for example cyclopropyl, cyclobutyl, cyclopentyl, cyclohexyl and cycloheptyl. "saturated heterocycle" denotes a saturated monocyclic group having 4 to 7 ring members, which contains 1 nitrogen atom and 1 other heteroatom selected from nitrogen (N), oxygen (O) and sulfur (S). Examples of suitable saturated heterocycles are azetidinyl, pyrrolidinyl, piperidinyl, morpholinyl, piperazinyl and azepanyl.

"het[1]" is defined in the present invention as a monocyclic or bicyclic heteroaromatic group having 5 to 10 ring members, which contains 1, 2, 3 or 4 heteroatom(s). The heteroatoms are selected from nitrogen (N), oxygen (O) and sulfur (S). In particular the heteroaromatic group contains either (a) 1 to 4 nitrogen atoms, (b) one oxygen atom or one sulfur atom or (c) 1 oxygen atom or 1 sulfur atom and 1 or 2 nitrogen atoms. Preferably the heteroaromatic group contains either from 1 to 4 ring nitrogen atom(s) or 1 or 2 nitrogen atoms and 1 oxygen atom. The heteroaromatic group is preferably C-linked, which means that the group is linked to the adjacent atom by a ring carbon atom. The heteroaromatic group can be unsubstituted, monosubstituted or disubstituted, as indicated in the definition of R[1] hereabove for general formula (I) and (I') according to the present invention. Substitution is preferably on a ring carbon atom. Examples of heteroaromatic groups include, but are not limited to: thiophenyl, furanyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyranyl, pyridinyl, pyrazinyl, pyrimidinyl, pyridazinyl, triazinyl, thiadiazinyl, isobenzofuranyl, benzofuranyl, chromenyl, indolizinyl, isoindolyl, indolyl, indazolyl, purinyl, quinolinyl, isoquinolyl, phthalazinyl, naphthyridinyl, quinazolinyl, quinoxalinyl, benzoxazolyl, benzothiazolyl, benzimidazolyl, benzofuranyl and benzothienyl.

According to a preferred aspect of the invention, het[1] is selected from monocyclic heteroaromatic groups having 5 or 6 ring members, which contain 1 to 2 nitrogen atoms or 1 nitrogen atom and 1 oxygen atom and bicyclic aromatic heteroaromatic groups having 9 or 10 ring members, which contain 1 to 4 nitrogen atoms or 1 nitrogen atom and 1 oxygen atom. More preferably, het[1] is selected from monocyclic heteroaromatic groups having 5 or 6 members, which contain from 1 to 2 nitrogen atoms. het[1] is preferably C-linked.

In the compounds of formula (I) or (I') R[4] and R[5] are preferably hydrogen or methyl and R[6] is preferably phenyl substituted by methoxy.

The one or two substituents on $R^1$ are preferably selected from
halogen,
$(C_1-C_4)$alkyl, optionally substituted by halogen
$(C_1-C_4)$alkoxy, optionally substituted by halogen
CN
morpholino
—$NR^2R^3$
—$C(O)NR^2R^3$
—$SO_2$—$NR^2R^3$
—$R^6$
—O—$R^6$
wherein $R^2$, $R^3$ and $R^6$ are as defined above.

More preferably, $R^1$ is unsubstituted or substituted by $(C_1-C_4)$alkyl, $(C_1-C_4)$alkoxy, $C(O)NR^2R^3$ or —$SO_2$—$NR^2R^3$, wherein $R^2$ and $R^3$ are independently from each other selected from hydrogen and $(C_1-C_4)$alkyl, preferably methyl According to a preferred aspect A is a group of formula

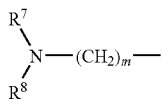

wherein m is 2 or 3, preferably 3 and $R^7$ and $R^8$ taken together with the N atom to which they are attached form a 5 or 6 membered saturated heterocycle, which is unsubstituted or substituted by one or two $(C_1-C_4)$alkyl, preferably methyl. More preferably $R^7$ and $R^8$ taken together with the N-atom to which they are attached form a 5 membered saturated heterocycle, which is unsubstituted or substituted by one or two methyl.

According to another preferred aspect A is a group of formula:

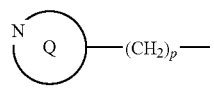

wherein p is 0 and Q is 6 membered saturated heterocycle, optionally substituted on the nitrogen atom by $(C_1-C_4)$alkyl, preferably isopropyl.

Specific preferred compounds according to the invention are those listed in the Examples section below, and more particularly:
7-pyridazin-3-yl-2-(3-pyrrolidin-1-ylpropoxy)-5,6,7,8-tetrahydro-1,7-naphthyridine,
6-pyrazin-2-yl-2-(3-pyrrolidin-1-ylpropoxy)-5,6,7,8-tetrahydro-1,6-naphthyridine,
6-(6-methylpyridin-3-yl)-2-(3-pyrrolidin-1-ylpropoxy)-5,6,7,8-tetrahydro-1,6-naphthyridine,
6-pyridazin-3-yl-2-(3-pyrrolidin-1-ylpropoxy)-5,6,7,8-tetrahydro-1,6-naphthyridine,
N-methyl-6-[2-(3-pyrrolidin-1-ylpropoxy)-7,8-dihydro-1,6-naphthyridin-6(5H)-yl]nicotinamide,
6-[2-(3-piperidin-1-ylpropoxy)-7,8-dihydro-1,6-naphthyridin-6(5H)-yl]nicotinamide,
2-(3-piperidin-1-ylpropoxy)-6-pyridazin-3-yl-5,6,7,8-tetrahydro-1,6-naphthyridine,
N,N-dimethyl-6-[2-(3-pyrrolidin-1-ylpropoxy)-7,8-dihydro-1,6-naphthyridin-6(5H)-yl]nicotinamide,
2-{3-[(2R)-2-methylpyrrolidin-1-yl]propoxy}-6-pyridazin-3-yl-5,6,7,8-tetrahydro-1,6-naphthyridine,
6-(6-methylpyridin-3-yl)-2-{3-[(2R)-2-methylpyrrolidin-1-yl]propoxy}-5,6,7,8-tetrrahydro-1,6-naphthyridine,
2-{3-[(2R)-2-methylpyrrolidin-1-yl]propoxy}-6-pyrazin-2-yl-5,6,7,8-tetrahydro-1,6-naphthyridine,
N-methyl-5-[2-(3-pyrrolidin-1-ylpropoxy)-7,8-dihydro-1,6-naphthyridin-6(5H)-yl]pyridine-2-carboxamide,
2-{3-[(2S)-2-methylpyrrolidin-1-yl]propoxy}-6-pyridazin-3-yl-5,6,7,8-tetrahydro-1,6-naphthyridine,
2-{3-[(2S)-2-methylpyrrolidin-1-yl]propoxy}-6-pyrazin-2-yl-5,6,7,8-tetrahydro-1,6-naphthyridine,
6-(6-methylpyridin-3-yl)-2-{3-[(2S)-2-methylpyrrolidin-1-yl]propoxy}-5,6,7,8-tetrahydro-1,6-naphthyridine,
N-methyl-6-[2-{3-[(2R)-2-methylpyrrolidin-1-yl]propoxy}-7,8-dihydro-1,6-naphthyridin-6(5H)-yl]nicotinamide,
2-[(1-isopropylpiperidin-4-yl)oxy]-6-pyrazin-2-yl-5,6,7,8-tetrahydro-1,6-naphthyridine,
N,N-dimethyl-5-[2-(3-pyrrolidin-1-ylpropoxy)-7,8-dihydro-1,6-naphthyridin-6(5H)-yl]pyridine-2-carboxamide,
N-methyl-5-[2-{3-[(2R)-2-methylpyrrolidin-1-yl]propoxy}-7,8-dihydro-1,6-naphthyridin-6(5H)-yl]pyridine-2-carboxamide,
N-methyl-6-[2-{3-[(2S)-2-methylpyrrolidin-1-yl]propoxy}-7,8-dihydro-1,6-naphthyridin-6(5H)-yl]nicotinamide,
2-[(1-isopropylpiperidin-4-yl)oxy]-6-(6-methylpyridin-3-yl)-5,6,7,8-tetrahydro-1,6-naphthyridine,
6-[2-[(1-isopropylpiperidin-4-yl)oxy]-7,8-dihydro-1,6-naphthyridin-6(5H)-yl]-N-methylnicotinamide,
5-[2-[(1-isopropylpiperidin-4-yl)oxy]-7,8-dihydro-1,6-naphthyridin-6(5H)-yl]-N-methylpyridine-2-carboxamide and
5-[2-(3-pyrrolidin-1-ylpropoxy)-7,8-dihydro-1,6-naphthyridin-6(5H)-yl]pyridine-2-carboxamide, and the pharmaceutically acceptable salts and solvates thereof.

Pharmaceutically acceptable salts of the compounds of formula (I) or formula (I') include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, Weinheim, Germany, 2002).

Pharmaceutically acceptable salts of compounds of formula (I) or formula (I') may be prepared by one or more of three methods:
(i) by reacting the compound of formula (I) or formula (I') with the desired acid or base;
(ii) by removing an acid- or base-labile protecting group from a suitable precursor of the compound of formula (I) or formula (I') or by ring-opening a suitable cyclic precursor, for example, a lactone or lactam, using the desired acid or base; or (iii) by converting one salt of the compound of formula (I) or formula (I') to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288, by Haleblian (August 1975).

Hereinafter all references to compounds of formula (I) or formula (I') include references to salts, solvates and complexes thereof and to solvates and complexes of salts thereof.

The compounds of the invention include compounds of formula (I) or formula (I') as hereinbefore defined, including all polymorphs and crystal habits thereof, prodrugs and isomers thereof (including optical, geometric and tautomeric isomers) as hereinafter defined and isotopically-labelled compounds of formula (I) or formula (I').

As indicated, so-called 'pro-drugs' of the compounds of formula (I) or formula (I') are also within the scope of the invention. Thus certain derivatives of compounds of formula (I) or formula (I') which may have little or no pharmacological activity themselves can, when administered into or onto the body, be converted into compounds of formula (I) or formula (I') having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (ed. E. B. Roche, American Pharmaceutical Association).

Prodrugs in accordance with the invention can, for example, be produced by replacing appropriate functionalities present in the compounds of formula (I) or formula (I') with certain moieties known to those skilled in the art as 'pro-moieties' as described, for example, in *Design of Prodrugs* by H. Bundgaard (Elsevier, 1985).

Some examples of prodrugs in accordance with the invention include:

(i) where the compound of formula (I) or formula (I') contains a carboxylic acid functionality (—COOH), an ester thereof, for example, a compound wherein the hydrogen of the carboxylic acid functionality of the compound of formula (I) or formula (I') is replaced by $(C_1-C_8)$alkyl;

(ii) where the compound of formula (I) or formula (I') contains an alcohol functionality (—OH), an ether thereof, for example, a compound wherein the hydrogen of the alcohol functionality of the compound of formula (I) or formula (I') is replaced by $(C_1-C_6)$alkanoyloxymethyl; and (iii) where the compound of formula (I) or formula (I') contains a primary or secondary amino functionality (—NH$_2$ or —NHR where R≠H), an amide thereof, for example, a compound wherein, as the case may be, one or both hydrogens of the amino functionality of the compound of formula (I) or formula (I') is/are replaced by $(C_1-C_{10})$alkanoyl.

Further examples of replacement groups in accordance with the foregoing examples and examples of other prodrug types may be found in the aforementioned references. Moreover, certain compounds of formula (I) or formula (I') may themselves act as prodrugs of other compounds of formula (I) or formula (I').

Also included within the scope of the invention are metabolites of compounds of formula (I) or formula (I'), that is, compounds formed in vivo upon administration of the drug. Some examples of metabolites in accordance with the invention include:

(i) where the compound of formula (I) or formula (I') contains a methyl group, an hydroxymethyl derivative thereof (—CH$_3$->—CH$_2$OH);

(ii) where the compound of formula (I) or formula (I') contains an alkoxy group, an hydroxy derivative thereof (—OR->—OH);

(iii) where the compound of formula (I) or formula (I') contains a tertiary amino group, a secondary amino derivative thereof (—NR$^a$R$^b$->—NHR$^a$ or —NHR$^b$);

(iv) where the compound of formula (I) or formula (I') contains a secondary amino group, a primary derivative thereof (—NHR$^a$->—NH$_2$);

(v) where the compound of formula (I) or formula (I') contains a phenyl moiety, a phenol derivative thereof (-Ph->-PhOH); and (vi) where the compound of formula (I) or formula (I') contains an amide group, a carboxylic acid derivative thereof (—CONR$^c$R$^d$->COOH).

Compounds of formula (I) or formula (I') containing one or more asymmetric carbon atoms can exist as two or more stereoisomers. Where structural isomers are interconvertible via a low energy barrier, tautomeric isomerism ('tautomerism') can occur. This can take the form of proton tautomerism in compounds of formula (I) or formula (I') containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (I) or formula (I'), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) or formula (I') contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Stereoisomeric conglomerates may be separated by conventional techniques known to those skilled in the art—see, for example, *Stereochemistry of Organic Compounds* by E. L. Eliel and S. H. Wilen (Wiley, New York, 1994).

The present invention includes all pharmaceutically acceptable isotopically-labelled compounds of formula (I) or formula (I') wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I) or formula (I'), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds of formula (I) or formula (I') can generally be prepared by conventional techniques known to those skilled in the art or by processes analogous to those described in the accompanying Examples and Preparations using an appropriate isotopically-labelled reagent in place of the non-labelled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

The compounds of the formula (I) and (I') according to the present invention can be prepared by the procedures described in the general methods presented below or by the specific methods described in the Examples section and the Preparations section, or by routine modifications thereof. The present invention also encompasses any one or more of these processes for preparing the compounds of formula (I) or formula (I'), in addition to any novel intermediates used therein.

Compounds of general formula (I) wherein A and $R^1$, are as defined above may be prepared according to reaction scheme 1:

Scheme 1

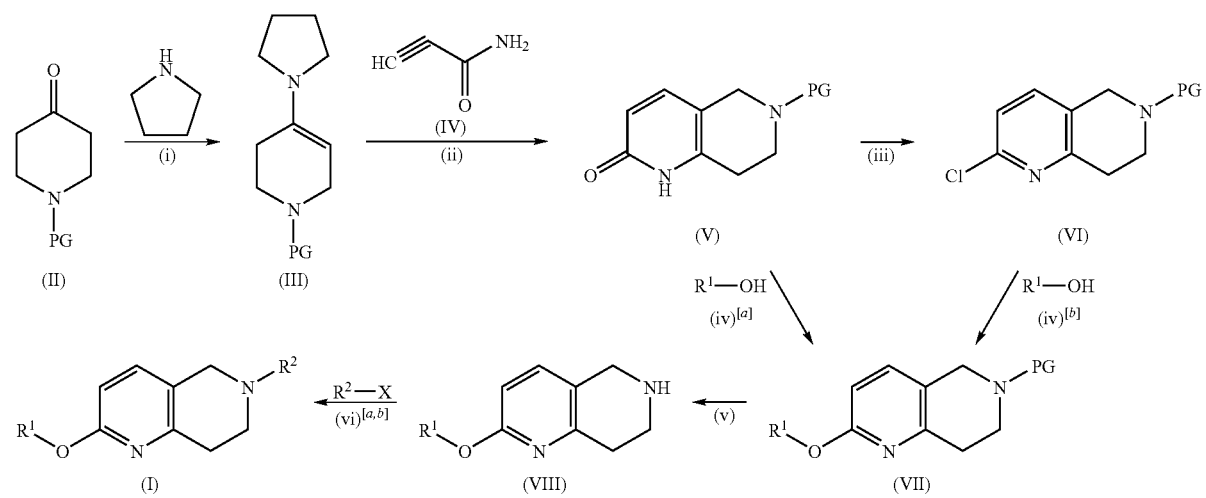

Compounds of general formula (II) are either commercially available or known in the literature. PG is a protecting group such as benzyl or allyl and is preferably benzyl. The use of protecting groups is described in "Protective Groups in Organic Synthesis", T. Greene and P. Wuts, 3$^{rd}$ edition, 1999, John Wiley and Sons.

Compounds of general formula (III) can be prepared from compounds of formula (II) by process step (i): reaction with pyrrolidine under Dean and Stark conditions with concomitant removal of water, at elevated temperature (e.g. 111-145° C.) in a suitable solvent such as toluene or xylene for 1-24 hours.

Alternatively compound (III) can be prepared under dehydrating conditions e.g. in the presence of a dehydrating agent such as molecular sieves or magnesium sulfate, in a suitable solvent such as tetrahydrofuran. Typical conditions comprise of 1 equivalent of compound (II) and 1-1.5 equivalents (molar) of pyrrolidine in toluene, heated under reflux with Dean and Stark conditions for 5 hours.

Compounds of general formula (V) can be prepared from compounds of general formula (III) by process step (ii): reaction with an excess of compound (IV) [*J. Amer. Chem. Soc.* 110(12), 3965-9; 1988], at elevated temperature (e.g. 111° C.) in a suitable solvent such as toluene, ethanol, xylene or tetrahydrofuran, for 1-24 hours. Typical conditions comprise of 1 equivalent of compound (III) and 1.5-2 equivalents of compound (IV) in toluene, heated under reflux and Dean and Stark conditions for 8 hours.

Alternatively compounds of formula (V) can be prepared from compounds of formula (III) by a two-step process involving sequential treatment with diethyl ethoxymethylenemalonate in dioxane at reflux, NH₄OAc and HCl at reflux (for PG=benzyl see EP588500) followed by decarboxylation at elevated temperatures (e.g. 220-240° C.) in a suitable solvent such as di(ethylene glycol).

Compounds of general formula (VI) can be prepared from compounds of general formula (V) by process step (iii): reaction with a suitable chlorinating agent such as phosphorous oxychloride/phosphorous pentachloride, optionally in the presence of a suitable base such as triethylamine and a suitable solvent such as dioxane, at elevated temperatures (e.g. up to 145° C.) for 1-24 hours. Typical conditions comprise of 1 equivalent of compound (V) and 1 equivalent of phosphorous pentachloride in excess phosphorous oxychloride heated under reflux for 3 hours.

Alternatively, compounds of general formula (VI) can be prepared as follows:

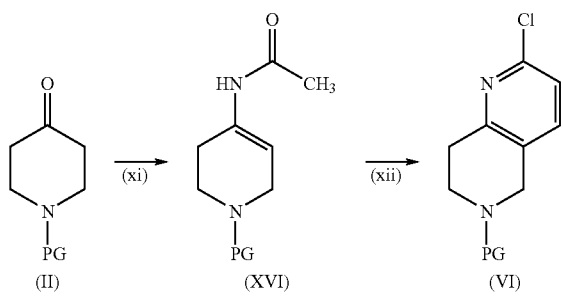

Compounds of general formula (XVI) can be prepared from compounds of formula (II) by process step (xi): reaction with acetamide under Dean and Stark conditions with concomitant removal of water, at elevated temperature, in the presence of a suitable acid such as para-toluenesulfonic acid or trifluoroacetic acid, in a suitable solvent such as xylene or toluene for 1-24 hours. Typical conditions comprise of 1.0 equivalent of compound (II), 1.0-3.0 equivalents of acetamide and 1.0-1.2 equivalents of para-toluenesulfonic acid in toluene, heated at 50° C. for 18 hours.

Compounds of general formula (VI) can be prepared from compounds of formula (XVI) by process step (xii): Vilsmeier-Haack type reaction in the presence of a suitable Vilsmeier reagent such as N,N-dimethylformamide or (Chloromethylene)dimethyliminium chloride, and phosphorus oxychloride, optionally in the presence of a suitable solvent such as dichloromethane, at elevated temperature, for 6-72 hours. Typical conditions comprise of 1.0 equivalent of compound (XVI), 1.0-1.2 equivalents of N,N-dimethylformamide and an excess of phosphorus oxychloride, heated at 75° C. for 6 hours.

Compounds of general formula (VII) can be prepared from compound (V) by process step (iv)[a]: a Mitsunobu reaction with a suitable alcohol A-OH in the presence of a suitable phosphine such as tri-ⁿbutyl phosphine or triphenyl phosphine and a suitable azo compound such as diethyl azodicarboxylate or 1'1'-azobis(N,N-dimethylformamide), in a suitable solvent such as toluene tetrahydrofuran or N,N-dimethylformamide, at elevated temperature for 1-48 hours. Typical conditions comprise of 1 equivalent of compound (V), 1.0-1.2 equivalents of A-OH, 1.0-1.2 equivalents of tri-ⁿbutyl phosphine and 1.0-1.2 equivalents of 1'1'-azobis(N, N-dimethylformamide) in toluene heated at 85° C. for 18 hours.

Preferably, compounds of general formula (VII) can be prepared from compounds of general formula (VI) by process step (iv)[b]: reaction with alcohol A-OH in the presence of a suitable base such as sodium hydride or potassium ᵗbutoxide in a suitable solvent such as tetrahydrofuran or N,N-dimethylformamide at elevated temperature (e.g. 67° C.) for 12-24 hours. Typical conditions comprise of 1.0 equivalent of compound (VI), 1-2 equivalents of potassium ᵗbutoxide and 1.0-1.5 equivalents of alcohol A-OH, in tetrahydrofuran, heated under reflux for 18 hours.

Compounds of formula (VIII) can be prepared from compounds of general formula (VII) by process step (v): deprotection of compound (VII) using standard methodology as described in "Protecting Groups in Organic Synthesis" by T. W. Greene and P. Wutz (see above). When PG is benzyl, typical conditions comprise of 1.0 equivalent of compound (VII), 5.0 equivalents of ammonium formate and 10% (w/w) Pd/C (catalyst) heated under reflux in ethanol, for 1 hour.

Compounds of formula (I) can be prepared from compounds of formula (VII) by process step (vi)[a]: reaction with halide R¹X, (where R¹ is as defined above and X is halo and preferably chloro or bromo), in the presence of a suitable base such as sodium ᵗbutoxide or triethylamine and a suitable catalyst system such as Pd₂(dba)₃ with BINAP, in a suitable solvent such as ᵗbutanol, heated at elevated temperature (e.g. 110° C.) in a microwave reaction heater. Typical conditions comprise of 1 equivalent of compound (VIII), 1-3 equivalents of R¹—X, 1.2-3.6 equivalents of sodium ᵗbutoxide, 5-15 mol % Pd₂(dba)₃ and 10-30 mol % BINAP in ᵗbutanol, at 110° C. for 0.5-3.0 hours.

Alternatively, compounds of formula (I) can be prepared from compounds of formula (VIII) by process step (vi)[b]: reaction with halide R¹X, (where R¹ is as defined above and X is halo and preferably chloro or bromo), optionally in the presence of a suitable base such potassium carbonate, sodium ᵗbutoxide or sodium carbonate, in a suitable solvent such as chlorobenzene, dimethylsulfoxide, or ᵗbutanol and NMP, at 25-150° C. for 1-48 hours. Typical conditions comprise of 1 equivalent of compound (VIII), 1-1.5 equivalents of R²X and 1-1.5 equivalents of potassium carbonate in chlorobenzene and NMP, heated under reflux for 24-48 hours.

Compounds of general formula (I') wherein A and R¹ are as defined above may be prepared according to reaction scheme 2:

Scheme 2

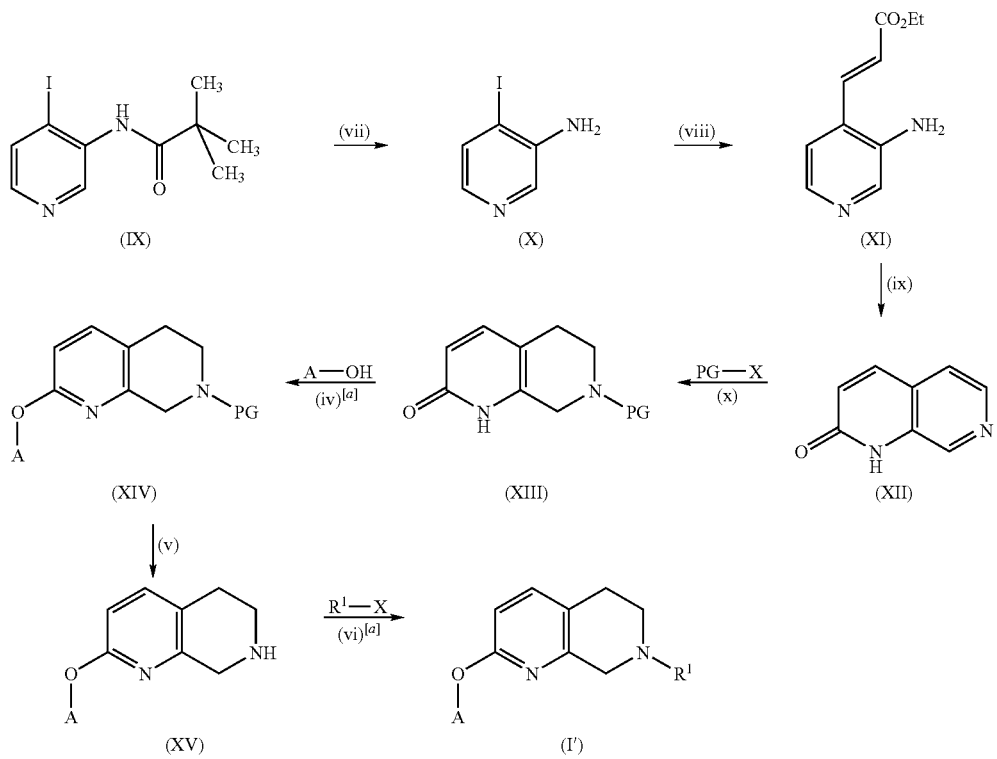

Compound (IX) can be prepared by analogy with the method of L. Estel et al (*J. Org. Chem.* 53(12), 2740-4; 1988).

Compound (X) can be prepared from compound (IX) by process step (vii): hydrolysis with a suitable acid such as sulphuric acid or hydrochloric acid, in a suitable solvent such as water or methanol, at elevated temperature (e.g. 100° C.) for 1-6 hours. Typical conditions comprise of 1 equivalent of compound (IX) in excess dilute sulphuric acid, heated under reflux for 1 hour.

Compound (XI) can be prepared from compound (X) by process step (viii): an analogous method to that of T. Sakamoto et al (*Chem. and Pharm. Bull.* 33(11) 4764-8; 1985). Typical conditions comprise of 1.0 equivalent of compound (X), 1.2 equivalent of ethyl acrylate, 10 mol % palladium acetate, 20 mol % tri-(O-tolyl) phosphine, and 1-1.5 equivalents of triethylamine in N,N-dimethylformamide at 80° C. for 3 hours.

Compound (XII) can be prepared from compound (XI) by process step (ix) as described in *Chem. and Pharm. Bull.* 33(11), 4764-8; 1985. Typical conditions comprise of 1 equivalent of compound (XI) and 4 equivalents of sodium ethoxide in ethanol heated under reflux for 1 hour.

Compounds of general formula (XIII) can be prepared from compound (XII) by process step (x): protection of N-atom with a suitable protecting agent such as allyl bromide or benzyl bromide, using standard methodology as described in "Protecting Groups in Organic Synthesis" by T. W. Greene and P. Wutz, followed by reduction with a suitable reducing agent such sodium borohydride, diisobutylammonium hydride or lithium aluminium hydride. Typical conditions comprise of 1 equivalent of compound (XII) and 1-1.5 equivalents of benzyl bromide, in ethanol, heated under reflux for 1-5 hours, followed by addition of 4.0-6.0 equivalents of sodium borohydride at 0-4° C. for 0-60 minutes.

Compounds of general formula (XIV) can be prepared from compounds of general formula (XIII) by process step (iv)[a] as described in scheme 1

Compounds of general formula (XV) can be prepared from compounds of general formula (XIV) by process step (v) as described in scheme 1.

Compounds of general formula (I) can be prepared from compounds of general formula (XV) by process step (vi)[a] as described in scheme 1.

All of the above reactions and the preparations of novel starting materials using in the preceding methods are conventional and appropriate reagents and reaction conditions for their performance or preparation as well as procedures for isolating the desired products will be well-known to those skilled in the art with reference to literature precedents and the examples and preparations hereto.

Compounds of the invention intended for pharmaceutical use may be administered as crystalline or amorphous products. They may be obtained, for example, as solid plugs, powders, or films by methods such as precipitation, crystallization, freeze-drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I) or formula (I'), a film-forming polymer, a binder, a solvent, a humectant, a plasticiser, a stabiliser or emulsifier, a viscosity-modifying agent and a solvent. Some components of the formulation may perform more than one function.

The compound of formula (I) or formula (I') may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) or formula (I') may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) or formula (I') used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I) or formula (I'), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 µg to 4000 µg of the compound of formula (I) or (I'). The overall daily dose will typically be in the range 1 µg to 20 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for wxample, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) or formula (I') in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the 0.001 mg to 2000 mg depending, of course, on the mode of administration. For example, oral administration may require a total daily dose of from 1 mg to 2000 mg, while an intravenous dose may only require from 0.01 mg to 100 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

For the avoidance of doubt, references herein to "treatment" include references to curative, palliative and prophylactic treatment.

According to another embodiment of the present invention, the compounds of the formula (I) or (I'), or pharmaceutically acceptable salts, derived forms or compositions thereof, can also be used as a combination with one or more additional therapeutic agents to be co-administered to a patient to obtain some particularly desired therapeutic end result. The second and more additional therapeutic agents may also be a compound of the formula (I) or (I'), or a pharmaceutically acceptable salt, derived forms or compositions thereof, or one or more histamine $H_3$ receptor ligands known in the art. More typically, the second and more therapeutic agents will be selected from a different class of therapeutic agents.

As used herein, the terms "co-administration", "co-administered" and "in combination with", referring to the compounds of formula (I) or (I') and one or more other therapeutic agents, is intended to mean, and does refer to and include the following:

simultaneous administration of such combination of compound(s) of formula (I) or (I') and therapeutic agent(s) to a patient in need of treatment, when such components are formulated together into a single dosage form which releases said components at substantially the same time to said patient, substantially simultaneous administration of such combination of compound(s) of formula (I) or (I') and therapeutic agent(s) to a patient in need of treatment, when such components are formulated apart from each other into separate dosage forms which are taken at substantially the same time by said patient, whereupon said components are released at substantially the same time to said patient, sequential administration of such combination compound (s) of formula (I) or (I') and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (I) or (I') and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Suitable examples of other therapeutic agents which may be used in combination with the compound(s) of formula (I) or (I'), or pharmaceutically acceptable salts, derived forms or compositions thereof, include, but are by no means limited to:

Histamine $H_1$ receptor antagonists, for instance loratidine, desloratidine, fexofenadine and cetirizine, Histamine $H_4$ receptor antagonists, Histamine $H_2$ receptor antagonists, Leukotriene antagonists, including antagonists of $LTB_4$, $LTC_4$, $LTD_4$, and $LTE_4$, in particular Montelukast, Phosphodiesterase inhibitors such as PDE4 inhibitors or PDE5 inhibitors, neurotransmitter re-uptake inhibitors, for instance fluoxetine, setraline, paroxetine, ziprasidone, 5-Lipoxygenase (5-LO) inhibitors or 5-lipoxygenase activating protein (FLAP) antagonists, $\alpha_1$- and $\alpha_2$-adrenoceptor agonist vasoconstrictor sympathomimetic agents for decongestant use, Muscarinic M3 receptor antagonists or anticholinergic agents, $\beta_2$-adrenoceptor agonists, Theophylline, Sodium cromoglycate, COX-1 inhibitors (NSAIDs) and COX-2 selective inhibitors, Oral or inhaled Glucocorticosteroids, Monoclonal antibodies active against endogenous inflammatory entities, Anti-tumor necrosis factor (anti-TNF-$\alpha$) agents, Adhesion molecule inhibitors including VLA-4 antagonists, Kinin-$B_1$- and $B_2$-receptor antagonists, Immunosuppressive agents, Inhibitors of matrix metalloproteases (MMPs), Tachykinin $NK_1$, $NK_2$ and $NK_3$ receptor antagonists, Elastase inhibitors, Adenosine A2a receptor agonists,
Inhibitors of urokinase,
Compounds that act on dopamine receptors, e.g. D2 agonists,
Modulators of the NFκβ pathway, e.g. IKK inhibitors,
Agents that can be classed as mucolytics or anti-tussive, antibiotics,
modulators of cytokine signalling pathways such as p38 MAP kinase, syk kinase or JAK kinase inhibitor,
HDAC inhibitors, and
PI3 kinase inhibitors.

According to the present invention, combination of the compounds of formula (I) or (I') with Histamine H1 receptor antagonists (e.g. loratidine, desloratidine, fexofenadine and cetirizine), Histamine $H_4$ receptor antagonists, Histamine $H_2$ receptor antagonists, Leukotriene antagonists, including antagonists of $LTB_4$, $LTC_4$, $LTD_4$, and $LTE_4$ (in particular Montelukast), Phosphodiesterase PDE4 inhibitors and neurotransmitter re-uptake inhibitors (e.g. fluoxetine, setraline, paroxetine, ziprasidone) are preferred.

The compounds of formula (I) or (I') have the ability to interact with the $H_3$ receptor and thereby have a wide range of therapeutic applications, as described further below, because of the essential role which the $H_3$ receptor plays in the physiology of all mammals. According to this invention $H_3$ ligands are meant to include $H_3$ receptor antagonists, agonists and inverse agonists. For the preferred indications to be treated according to the invention, $H_3$ antagonists are believed to be most suitable.

Therefore, a further aspect of the present invention relates to the compounds of formula (I) or (I'), or pharmaceutically acceptable salts, derived forms or compositions thereof, for use in the treatment of diseases, disorders, and conditions in which the $H_3$ receptor is involved. More specifically, the present invention also concerns the compounds of formula (I) or (I'), or pharmaceutically acceptable salts, derived forms or compositions thereof, for use in the treatment of diseases, disorders, and conditions selected from the group consisting of:
  diseases of the central nervous system: sleep disorders, migraine, dyskinesia, stress-induced anxiety, psychotic disorders, epilepsy, Cognition deficiency diseases such as Alzheimer's disease or mild cognitive impairment, depression, mood disorders, schizophrenia, anxiety disorders, attention-deficit hyperactivity disorder (ADHD), psychotic disorders, obesity, dizziness, vertigo, epilepsy, motion sickness
  inflammatory diseases
  respiratory diseases (adult respiratory distress syndrome, acute respiratory distress syndrome, bronchitis, chronic bronchitis, chronic obstructive pulmonary disease, cystic fibrosis, asthma, emphysema, rhinitis, chronic sinusitis), allergy, allergy-induced airway responses, allergic rhinitis, viral rhinitis, non-allergic rhinitis, perennial and seasonal rhinitis, nasal congestion, allergic congestion
  Female sexual dysfunction including hypoactive sexual desire disorder, sexual arousal disorder, orgasmic disorder and sexual pain disorder
  Male sexual dysfunction including male desire disorders, male erectile dysfunction, male orgasmic disorders such as premature ejaculation
  cardiac dysfunctions such as myocardial ischaemia and arrythmia
  diseases of the gastrointestinal tract such as inflammatory bowel disease, Crohn's disease and colitis ulcerosa
  cancer
  hypotension
  pain and
  overactive bladder conditions The compounds of formula (I) or (I') of the invention are particularly suitable for the treatment of allergy, allergy-induced airway responses, allergic rhinitis, viral rhinitis, non-allergic rhinitis, perennial and seasonal rhinitis, nasal congestion and allergic congestion.

A still further aspect of the present invention also relates to the use of the compounds of formula (I) or (I'), or pharmaceutically acceptable salts, derived forms or compositions thereof, for the manufacture of a drug being a $H_3$ ligand. In particular, the present inventions concerns the use of the compounds of formula (I) or (I'), or pharmaceutically acceptable salts, derived forms or compositions thereof, for the manufacture of a drug for the treatment of H3-mediated diseases and/or conditions, in particular the diseases and/or conditions listed above.

As a consequence, the present invention provides a particularly interesting method to treat a mammal, including a human being, with an effective amount of a compound of formula (I) or (I'), or a pharmaceutically acceptable salt, derived form or composition thereof. More precisely, the present invention provides a particularly interesting method for the treatment of a H3-mediated diseases and/or conditions in a mammal, including a human being, in particular the diseases and/or conditions listed above, comprising administering to said mammal an effective amount of a compound of formula (I) or (I'), its pharmaceutically acceptable salts and/or or derived forms.

The following examples illustrate the preparation of the compounds of formula (I) and (I') according to the present invention.

EXAMPLE SECTION

[1]H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (m/z) were recorded using either electrospray ionisation (ESI) or atmospheric pressure chemical ionisation (APCI). The following abbreviations have been used: $Pd_2(dba)_3$ is tris(dibenzylideneacetone)dipalladium, BINAP is 2,2'-bis(diphenylphosphino)-1,1'-binapthyl, TMEDA is N,N,N'N'-tetramethylethylene diamine, NMP is 1-methyl-2-pyrrolidinone. 'Ammonia' refers to a concentrated solution of ammonia in water possessing a specific gravity of 0.88. Where thin layer chromatography (TLC) has been used it refers to silica gel TLC using silica gel 60 $F_{254}$ plates, $R_f$ is the distance travelled by a compound divided by the distance travelled by the solvent front on a TLC plate. Microwave equipment is Personal Chemistry Emrys Liberator, or Personal Chemistry Smith Creator.

Example 1

6-Pyrimidin-2-yl-2-(3-pyrrolidin-1-ylpropoxy)-5,6,7,8-tetrahydro-1,6-naphthyridine

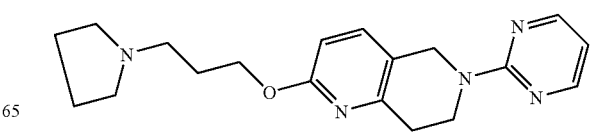

The product of preparation 16 (80 mg, 0.31 mmol) and 2-bromopyrimidine (49 mg, 0.31 mmol) were mixed together in t-butanol (8 mL) and stirred at 25° C. for 12 hours. The temperature was then increased to 45° C. and the reaction mixture was stirred for 7 hours, with additional 2-bromopyrimidine (5 mg) being added after 3 hours. The solvent was then evaporated under reduced pressure and the residue was purified by column chromatography on silica gel, eluting with ethyl acetate:pentane: 0.88 ammonia, 20:80:1 to 60:40:1, followed by dichloromethane:methanol: 0.88 ammonia, 100:0:1 to 90:10:1, to yield a white solid. Re-crystallisation of the solid from cyclohexane afforded the title compound as a white solid in 24% yield, 25 mg.

$^1$HNMR(CDCl$_3$, 400MHz) δ: 1.70-1.90 (m, 4H), 2.00-2.10 (m, 2H), 2.47-2.75 (m, 6H), 2.93-3.00 (m, 2H), 4.18 (m, 2H), 4.35 (m, 2H), 4.80 (s, 2H), 6.50-6.60 (m, 2H), 7.38 (m, 1H), 8.39 (d, 2H)

MS APCI+ m/z 340 [MH]$^+$

Example 2

6-Pyridin-2-yl-2-(3-pyrrolidin-1-ylpropoxy)-5,6,7,8-tetrahydro-1,6-naphthyridine

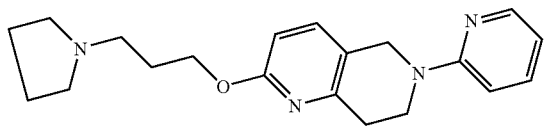

A mixture of the product of preparation 16 (68 mg, 0.26 mmol), 2-bromopyridine (62 mg, 0.39 mmol), sodium tert-butoxide, (30 mg, 0.31 mmol), Pd$_2$(dba)$_3$ (4 mg, 4 μmol) and BINAP (9 mg, 14 μmol) were suspended in tert-butanol (2 mL) and the mixture was heated at 110° C. in the microwave for 30 minutes. The reaction mixture was then dissolved in methanol, filtered and concentrated in vacuo. The residue was purified by column chromatography on silica gel, eluting with dichloromethane:methanol:0.88 ammonia, 100:0:0 to 80:20:1, to afford the title compound in 64% yield, 57 mg.

$^1$HNMR(CDCl$_3$, 400 MHz) δ: 1.70-1.90 (m, 4H), 1.92-2.10 (m, 2H), 2.47-2.72 (m, 6H), 2.90-3.00 (m, 2H), 3.90 (m, 2H), 4.30 (m, 2H), 4.60 (s, 2H), 6.59-6.70 (m, 2H), 6.86 (d, 1H), 7.45-7.60 (m, 2H), 8.10 (m, 1H)

MS APCI+ m/z 339 [MH]$^+$

Example 3

6-Pyrazin-2-yl-2-(3-pyrrolidin-1-ylpropoxy)-5,6,7,8-tetrahydro-1.6-naphthyridine

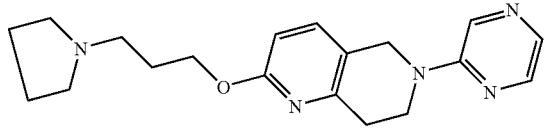

The product of preparation 16 (83 mg, 0.32 mmol), 2-chloropyrazine (36 mg, 0.31 mmol), sodium tert-butoxide, (36 mg, 0.37 mmol), Pd$_2$(dba)$_3$ (7 mg, 8 μmol) and BINAP (22 mg, 35 μmol) were suspended in tert-butanol (2 mL) and the mixture was heated at 110° C. in the microwave for 3 hours. The mixture was replenished with further amounts of 2-chloropyrazine (36 mg, 0.31 mmol), sodium tert-butoxide (36 mg, 0.37 mmol), Pd$_2$(dba)$_3$ (7 mg, 8 μmol) and BINAP (22 mg, 30 μmol) at hourly intervals. The reaction mixture was then azeotroped with methanol and concentrated in vacuo. The residue was purified by column chromatography on silica gel, eluting with ethyl acetate:methanol: 0.88 ammonia, 100:0:0 to 90:10:1. This was followed by further purification by column chromatography on Biotage® amino silica gel, eluting with pentane:ethyl acetate, 100:0 to 0:100, to afford the title compound as a colourless oil in 76% yield, 80 mg.

$^1$HNMR(CDCl$_3$, 400 MHz) δ: 1.70-1.90 (m, 4H), 1.91-2.04 (m, 2H), 2.47-2.63 (m, 6H), 2.93-3.02 (m, 2H), 3.90-3.98 (m, 2H) 4.28-4.35 (m, 2H), 4.63 (s, 2H), 6.60 (d, 1H), 7.37 (d, 1H), 7.85 (m, 1H), 8.10 (m, 1H), 8.21 (m,1 H)

MS APCI+ m/z 340 [MH]$^+$

Micro analysis found (%); C(67.21); H(7.46); N(20.60); C$_{19}$H$_{25}$N$_5$O requires (%); C(67.31); H(7.42); N(20.63)

Examples 4 to 32

The following compounds of the general formula shown below were prepared from the product of preparations 16, 17, 18, 19, 20, 21 and 28 and the appropriate heterocyclic halide: R$^1$Cl or R$^1$Br. A method similar to that described for example 3 was utilised where by the reaction mixture was heated in a microwave at 110° C. for 1-3 hours. The progress of the reactions were monitored by tlc and the reaction mixture was treated with further amounts of heterocyclic halide, sodium tert-butoxide, Pd$_2$(dba)$_3$ and BINAP at regular intervals until all of the starting material had been consumed.

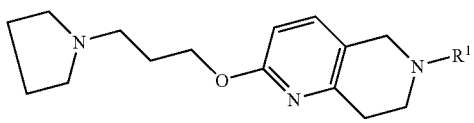

| No. | R$^1$ | Data | Yield |
|---|---|---|---|
| 4 | 6-(3-methylpyridin-2-yl)-2-(3-pyrrolidin-1-ylpropoxy)-5,6,7,8-tetrahydro-1,6-naphthyridine 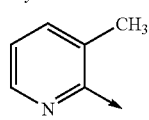 | $^1$HNMR(CDCl$_3$, 400 MHz) δ: 1.70-1.90(brm, 4H), 1.98-2.06(m, 2H), 2.30(s, 3H), 2.50-2.68(brm, 6H), 2.93-3.02(m, 2H), 3.40-3.44(m, 2H) 4.28-4.35(m, 4H), 6.59(d, 1H), 6.85(m, 1H), 7.36(d, 1H), 7.42(m, 1H), 8.19(m, 1H)<br>MS APCI+<br>m/z 353[MH]$^+$ | 28% |

-continued

| No. | R¹ | Data | Yield |
|---|---|---|---|
| 5 | 6-(6-methylpyridin-3-yl)-2-(3-pyrrolidin-1-ylpropoxy)-5,6,7,8-tetrahydro-1,6-naphthyridine 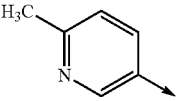 | ¹HNMR(CDCl₃, 400 MHz) δ: 1.70-1.90(brm, 4H), 1.98-2.06(m, 2H), 2.42-2.68(brm, 9H), 2.93-3.02(m, 2H), 3.60(m, 2H), 4.22-4.35(m, 4H), 6.59(d, 1H), 7.01(d, 1H), 7.20(m, 1H), 7.39(d, 1H), 8.22(m, 1H) MS APCI+ m/z 353[MH]⁺ | 30% |
| 6 | 2-(3-pyrrolidin-1-ylpropoxy)-6-[5-(trifluoromethyl)pyridin-2-yl]-5,6,7,8-tetrahydro-1,6-naphthyridine 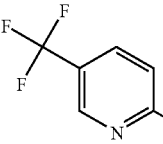 | ¹HNMR(CDCl₃, 400 MHz) δ: 1.70-1.90(brm, 4H), 1.85-2.06(m, 2H), 2.45-2.62(brm, 6H), 2.93-3.02(m, 2H), 3.98(m, 2H), 4.30(m, 2H), 4.64(s, 2H), 6.59(d, 1H), 6.70(d, 1H), 7.38(d, 1H), 7.63(m, 1H) 8.41(s, 1H) MS APCI+ m/z 407[MH]⁺ | 71% |
| 7 | 2-(3-pyrrolidin-1-ylpropoxy)-6-[6-(trifluoromethyl)pyridin-2-yl]-5,6,7,8-tetrahydro-1,6-naphthyridine 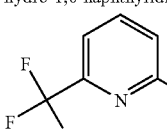 | ¹HNMR(CDCl₃, 400 MHz) δ: 1.70-1.90(brm, 4H), 1.98-2.06(m, 2H), 2.50-2.68(brm, 6H), 2.93-3.02(m, 2H), 3.84-3.95(m, 2H), 4.28-4.35(m, 2H), 4.65(s, 2H), 6.53(d, 1H), 6.83(m, 2H), 6.95(m, 1H) 7.39(d, 1H), 7.60(m, 1H) MS APCI+ m/z 407[MH]⁺ | 31% |
| 8 | 2-(3-pyrrolidin-1-ylpropoxy)-6-[4-(trifluoromethyl)pyridin-2-yl]-5,6,7,8-tetrahydro-1,6-naphthyridine 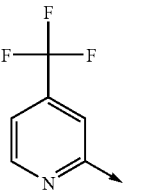 | ¹HNMR(CDCl₃, 400 MHz) δ: 1.70-1.90(brm, 4H), 1.98-2.02(m, 2H), 2.41-2.61(brm, 6H), 2.96(m, 2H), 3.96(m, 2H), 4.53(m, 2H), 4.62(s, 2H), 6.60(d, 1H), 6.80(m, 2H), 7.38(d, 1H), 8.39(d, 1H) MS APCI+ m/z 407[MH]⁺ | 13% |
| 9 | 2-(3-pyrrolidin-1-ylpropoxy)-6-[6-(2,2,2-trifluoroethoxy)pyridin-2-yl]-5,6,7,8-tetrahydro-1,6-naphthyridine 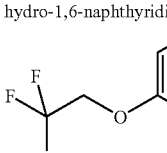 | ¹HNMR(CDCl₃, 400 MHz) δ: 1.65-1.82(brm, 4H), 1.91-2.01(m, 2H), 2.45-2.62(brm, 6H), 2.93-3.00(m, 2H), 3.90(m, 2H), 4.30(m, 2H), 4.59(s, 2H), 4.75(m, 2H), 6.08(d, 1H), 6.20(d, 1H), 6.58(d, 1H), 7.38-7.42(m, 2H) MS APCI+ m/z 437[MH]⁺ | 55% |
| 10 | 6-(5-fluoropyridin-2-yl)-2-(3-pyrrolidin-1-ylpropoxy)-5,6,7,8-tetrahydro-1,6-naphthyridine 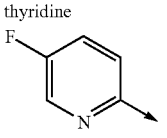 | ¹HNMR(CDCl₃, 400 MHz) δ: 1.85-1.90(m, 4H), 1.95-2.06(m, 2H), 2.45-2.70(brm, 6H), 2.93-3.02(m, 2H), 3.98(m, 2H), 4.30(m, 2H), 4.58(s, 2H), 6.59(d, 1H), 6.70(m, 1H), 7.20-7.40(m, 2H), 8.03(m, 1H) MS APCI+ m/z 357[MH]⁺ | 52% |
| 11 | 6-(6-methoxypyridin-2-yl)-2-(3-pyrrolidin-1-ylpropoxy)-5,6,7,8-tetrahydro-1,6-naphthyridine 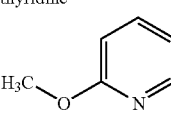 | ¹HNMR(CDCl₃, 400 MHz) δ: 1.70-1.82(m, 4H), 1.91-2.01(m, 2H), 2.45-2.62(brm, 6H), 2.93-3.00(m, 2H), 3.90(m, 5H), 4.30(m, 2H), 4.59(s, 2H), 6.08(d, 1H), 6.20(d, 1H), 6.58(d, 1H), 7.38-7.42(m, 2H) MS APCI+ m/z 369[MH]⁺ | 85% |

-continued

| No. | R¹ | Data | Yield |
|---|---|---|---|
| 12 | 2-(3-pyrrolidin-1-ylpropoxy)-6-quinolin-2-yl-5,6,7,8-tetrahydro-1,6-naphthyridine 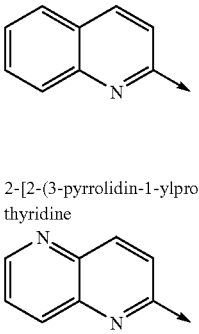 | ¹HNMR(CDCl₃, 400 MHz) δ: 2.03-2.20(brm, 4H), 2.30-2.45(m, 2H), 3.00-3.35(brm, 8H), 4.05(m, 2H), 4.40(m, 2H), 4.82(s, 2H), 6.60(d, 1H), 7.05(d, 1H), 7.30(m, 1H), 7.41(m, 1H), 7.50-7.62(m, 2H) 7.79(m, 1H), 7.95(m, 1H)<br>MS APCI+ m/z 389[MH]⁺ | 23% |
| 13 | 2-[2-(3-pyrrolidin-1-ylpropoxy)-7,8-dihydro-1,6-naphthyridin-6(5H)-yl]-1,5-naphthyridine 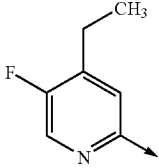 | ¹HNMR(CDCl₃, 400 MHz) δ: 1.98-2.18(brm, 4H), 2.22-2.40(m, 2H), 2.98-3.24(brm, 8H), 4.05(m, 2H), 4.35(m, 2H), 4.80(s, 2H), 6.60(d, 1H), 7.21(m, 1H), 7.38(m, 2H), 8.00(d, 1H), 8.17(d, 1H), 8.60(m, 1H)<br>MS APCI+ m/z 390[MH]⁺ | 6% |
| 14 | 6-(4-ethyl-5-fluoropyridin-2-yl)-2-(3-pyrrolidin-1-ylpropoxy)-5,6,7,8-tetrahydro-1,6-naphthyridine 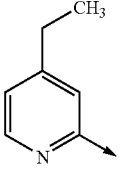 | ¹HNMR(CDCl₃, 400 MHz) δ: 1.22(t, 3H), 1.70-1.90(brm, 4H), 2.06-2.20(m, 2H), 2.05-2.65(brm, 8H), 3.00(m, 2H), 3.80(m, 2H), 4.37(m, 2H), 4.58(s, 2H), 6.57(m, 2H), 7.38(m, 1H), 7.99(s, 1H)<br>MS APCI+ m/z 385[MH]⁺ | 36% |
| 15 | 6-(4-ethylpyridin-2-yl)-2-(3-pyrrolidin-1-ylpropoxy)-5,6,7,8-tetrahydro-1,6-naphthyridine 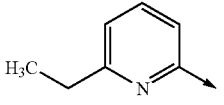 | ¹HNMR(CDCl₃, 400 MHz) δ: 1.20(t, 3H), 1.70-1.90(brm, 4H), 1.98-2.02(m, 2H), 2.43-2.63(brm, 8H), 2.96(m, 2H), 3.80-4.00(m, 2H), 4.30(m, 2H), 4.58(s, 2H), 6.24-6.40(m, 3H), 7.38(m, 1H), 8.02(m, 1H)<br>MS APCI+ m/z 367[MH]⁺ | 26% |
| 16 | 6-(6-ethylpyridin-2-yl)-2-(3-pyrrolidin-1-ylpropoxy)-5,6,7,8-tetrahydro-1,6-naphthyridine 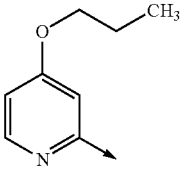 | ¹HNMR(CDCl₃, 400 MHz) δ: 1.22(t, 3H), 1.70-1.82(m, 4H), 1.98-2.03(m, 2H), 2.45-2.70(brm, 8H), 2.93-3.02(m, 2H), 3.90-3.98(m, 2H) 4.28-4.35(m, 2H), 4.61(s, 2H), 6.50-6.60(m, 3H), 7.37-7.42(m, 2H)<br>MS APCI+ m/z 367[MH]⁺ | 67% |
| 17 | 6-(4-propoxypyridin-2-yl)-2-(3-pyrrolidin-1-ylpropoxy)-5,6,7,8-tetrahydro-1,6-naphthyridine 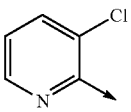 | ¹HNMR(CDCl₃, 400 MHz) δ: 1.00(t, 3H), 1.70-1.90(brm, 6H), 1.98-2.02(m, 2H), 2.41-2.61(brm, 6H), 2.96(m, 2H), 3.80-4.00(m, 4H), 4.30(m, 2H), 4.58(s, 2H), 6.19(s, 1H), 6.20(m, 1H), 6.59(d, 1H), 7.38(m, 1H), 8.00(m, 1H)<br>MS APCI+ m/z 397 [MH]⁺ | 55% |
| 18 | 6-(3-chloropyridin-2-yl)-2-(3-pyrrolidin-1-ylpropoxy)-5,6,7,8-tetrahydro-1,6-naphthyridine | ¹HNMR(CDCl₃, 400 MHz) δ: 1.70-1.85(m, 2H), 1.95-2.05(m, 4H), 2.45-2.63(brm, 6H), 3.03(m, 2H), 3.70(m, 2H), 4.28-4.35(m, 2H), 4.42(s, 2H), 6.57(d, 1H), 6.81(m, 1H), 7.39(d, 1H), 7.60(m, 1H), 8.20(m, 1H)<br>MS APCI+ m/z 373[MH]⁺ | 22% |

| No. | R¹ | Data | Yield |
|---|---|---|---|
| 19 | N,N-dimethyl-6-[2-(3-pyrrolidin-1-ylpropoxy)-7,8-dihydro-1,6-naphthyridin-6(5H)-yl]pyridin-2-amine 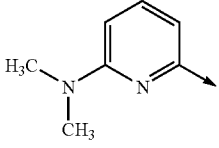 | ¹HNMR(CDCl₃, 400 MHz) δ: 1.70-1.84(m, 4H), 1.91-2.01(m, 2H), 2.45-2.62(brm, 6H), 2.93-3.00(m, 2H), 3.10(s, 6H), 3.90(m, 2H), 4.30(m, 2H), 4.59(s, 2H), 5.92(d, 1H), 6.00(d, 1H), 6.58(d, 1H), 7.38-7.42(m, 2H)<br>MS APCI+ m/z 382[MH]⁺ | 82% |
| 20 | N,N-dimethyl-6-[2-(3-pyrrolidin-1-ylpropoxy)-7,8-dihydro-1,6-naphthyridin-6(5H)-yl]pyridine-2-sulfonamide 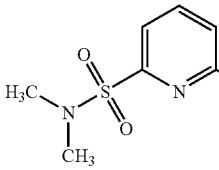 | ¹HNMR(CDCl₃, 400 MHz) δ: 1.83-2.00(m, 4H), 2.10-2.22(m, 2H), 2.65-3.01(brm, 14H), 3.98(m, 2H), 4.35(m, 2H), 4.61(s, 2H), 5.60(d, 1H), 6.81(m, 1H), 7.21(m, 1H), 7.38(d, 1H), 7.63(m, 1H)<br>MS APCI+ m/z 446[MH]⁺ | 24% |
| 21 | 6-pyridazin-3-yl-2-(3-pyrrolidin-1-ylpropoxy)-5,6,7,8-tetrahydro-1,6-naphthyridine 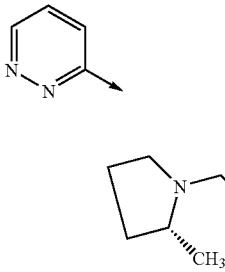 | ¹HNMR(CDCl₃, 400 MHz) δ: 1.70-1.82(m, 4H), 1.98-2.03(m, 2H), 2.45-2.70(brm, 6H), 2.97-3.02(m, 2H), 3.95(m, 2H), 4.35(m, 2H), 4.76(s, 2H), 6.60(d, 1H), 6.98(m, 1H), 7.22(m, 1H), 7.39(d, 1H), 8.60(m, 1H)<br>MS APCI+ m/z 340[MH]⁺ | 43% |

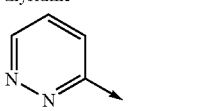

| No. | R¹ | Data | Yield |
|---|---|---|---|
| 22 | 2-{3-[(2R)-2-methylpyrrolidin-1-yl]propoxy}-6-pyridazin-3-yl-5,6,7,8-tetrahydro-1,6-naphthyridine 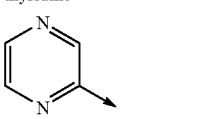 | ¹HNMR(CD₃OD, 400 MHz) δ: 1.14(d, 3H), 1.43(m, 1H), 1.78(m, 2H), 1.96-2.04(m, 3H), 2.26(m, 2H), 2.42(m, 1H), 2.96(t, 2H), 3.05(m, 1H), 3.21(m, 1H), 4.00(t, 2H), 4.30(t, 2H), 4.71(s, 2H), 6.64(d, 1H), 7.35(m, 1H), 7.43(m, 1H), 7.55(m, 1H), 8.49(m, 1H)<br>MS ES+ m/z 354[MH]⁺<br>[α]_D = −40(c = 0.185 in MeOH, 95% ee) | 62% |
| 23 | 2-{3-[(2R)-2-methylpyrrolidin-1-yl]propoxy}-6-pyrazin-2-yl-5,6,7,8-tetrahydro-1,6-naphthyridine 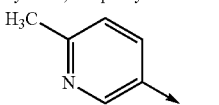 | ¹HNMR(CD₃OD, 400 MHz) δ: 1.12(d, 3H), 1.44(m, 1H), 1.77(m, 2H), 1.93-2.04(m, 3H), 2.22(m, 2H), 2.42(m, 1H), 2.95(t, 2H), 3.05(m, 1H), 3.21(m, 1H), 3.99(t, 2H), 4.30(t, 2H), 4.67(s, 2H), 6.65(d, 1H), 7.53(d, 1H), 7.79(m, 1H), 8.12(m, 1H), 8.27(d, 1H)<br>MS ES+ m/z 354[MH]⁺<br>[α]_D = −54(c = 0.140 in MeOH, 95% ee) | 63% |
| 24 | 6-(6-methylpyridin-3-yl)-2-{3-[(2R)-2-methylpyrrolidin-1-yl]propoxy}-5,6,7,8-tetrahydro-1,6-naphthyridine | ¹HNMR(CD₃OD, 400 MHz) δ: 1.11(d, 3H), 1.43(m, 1H), 1.78(m, 2H), 1.91-2.02(m, 3H), 2.22(m, 2H), 2.40(m, 1H), 2.41(s, 3H), 2.95(t, 2H), 3.03(m, 1H), 3.19(m, 1H), 3.62(t, 2H), 4.28-4.34(m, 4H), 6.63(d, 1H), 7.16(d, 1H), 7.43(m, 1H), 7.50(d, 1H), 8.26(d, 1H)<br>MS ES+ m/z 367[MH]⁺<br>[α]_D = −44(c = 0.160 in MeOH, 95% ee) | 46% |

| No. | R¹ | Data | Yield |
|---|---|---|---|

-continued

[Structure: (2S)-2-methylpyrrolidine-N-propoxy-tetrahydro-1,6-naphthyridine with N-R¹]

| 25 | 2-{3-[(2S)-2-methylpyrrolidin-1-yl]propoxy}-6-pyridazin-3-yl-5,6,7,8-tetrahydro-1,6-naphthyridine | | |
|---|---|---|---|
| 25 | [pyridazin-3-yl structure] | ¹HNMR(CDCl₃, 400 MHz) δ: 1.10(d, 3H), 1.45(m, 1H), 1.70(m, 3H), 1.95(m, 3H), 2.25(m, 2H), 2.99(m, 3H), 3.21(m, 1H), 3.96(t, 2H), 4.35(t, 2H), 4.77(s, 2H), 6.60(d, 1H), 6.97(d, 1H), 7.22(m, 1H), 7.38(m, 1H), 8.60(m, 1H) MS APCI+ m/z 354[MH]⁺ [α]_D = +46(c = 0.115 in MeOH, 90% ee) | 41% |
| 26 | 2-{3-[(2S)-2-methylpyrrolidin-1-yl]propoxy}-6-pyrazin-2-yl-5,6,7,8-tetrahydro-1,6-naphthyridine | | |
| | [pyrazin-2-yl structure] | ¹HNMR(CDCl₃, 400 MHz) δ: 1.09(d, 3H), 1.41(m, 1H), 1.60-1.80(m, 2H), 1.83-2.30(m, 6H), 2.99(m, 3H), 3.20(m, 1H), 3.96(t, 2H), 4.35(t, 2H), 4.64(s, 2H), 6.61(d, 1H), 7.39(d, 1H), 7.86(m, 1H), 8.10(m, 1H), 8.22(s, 1H) MS APCI+ m/z 354[MH]⁺ [α]_D = +43(c = 0.105 in MeOH, 90% ee) | 64% |
| 27 | 6-(6-methylpyridin-3-yl)-2-{3-[(2S)-2-methylpyrrolidin-1-yl]propoxy}-5,6,7,8-tetrahydro-1,6-naphthyridine | | |
| | [6-methylpyridin-3-yl structure] | ¹HNMR(CDCl₃, 400 MHz) δ: 1.15(d, 3H), 1.45(m, 1H), 1.78-1.81(m, 2H), 1.88-2.10(m, 3H), 2.20-2.38(m, 2H), 2.42(s, 4H), 2.93-3.00(m, 2H), 3.01-3.10(m, 1H), 3.20-3.39(s, 1H), 3.60-3.65(m, 2H), 4.30-4.38(m, 4H), 6.61(d, 1H), 7.19(d, 1H), 7.42(m, 1H), 7.53(d, 1H), 8.19(d, 1H) MS APCI+ m/z 354[MH]⁺ [α]_D = +42(c = 0.145 in MeOH, 90% ee) | 35% |

[Structure: (2R,5R)-2,5-dimethylpyrrolidine-N-propoxy-tetrahydro-1,6-naphthyridine with N-R¹]

| 28 | 2-{3-[(2R,5R)-2,5-dimethylpyrrolidin-1-yl]propoxy}-6-(6-methylpyridin-3-yl)-5,6,7,8-tetrahydro-1,6-naphthyridine | | |
|---|---|---|---|
| | [6-methylpyridin-3-yl structure] | ¹HNMR(CDCl₃, 400 MHz) δ: 0.96(d, 6H), 1.28-1.42(m, 2H), 1.88-2.03(m, 4H), 2.40-2.58(m, 4H), 2.80(m, 1H), 2.98-3.10(m, 4H), 3.59(m, 2H), 4.20-4.38(m, 4H), 6.59(d, 1H), 7.02(d, 1H), 7.20(m, 1H), 7.33(d, 1H), 8.22(d, 1H) MS APCI+ m/z 381[MH]⁺ | 11% |

[Structure: piperidine-N-propoxy-tetrahydro-1,6-naphthyridine with N-R¹]

| 29 | 2-(3-piperidin-1-ylpropoxy)-6-pyridazin-3-yl-5,6,7,8-tetrahydro-1,6-naphthyridine | | |
|---|---|---|---|
| | [pyridazin-3-yl structure] | ¹HNMR(CDCl₃, 400 MHz) δ: 1.20-1.30(m, 2H), 1.30-1.70(brm, 4H), 1.90-2.05(m, 2H), 2.30-2.50(brm, 6H), 2.95-3.05(m, 2H), 3.90-4.00(m, 2H), 4.25-4.35(m, 2H), 4.77(s, 2H), 6.60(d, 1H), 6.98(d, 1H), 7.22(m, 1H), 7.39(d, 1H), 8.60(d, 1H) MS APCI+ m/z 354[MH]⁺ | 35% |

| No. | R¹ | Data | Yield |
|---|---|---|---|
| | 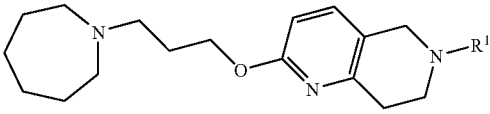 | | |
| 30 | 2-(3-azepan-1-ylpropoxy)-6-pyridazin-3-yl-5,6,7,8-tetrahydro-1,6-naphthyridine <br> 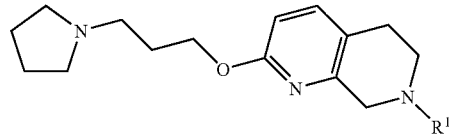 | ¹HNMR(CDCl₃, 400 MHz) δ: 1.40-1.80(m, 8H), 1.85-2.05(m, 2H), 2.50-2.80(m, 6H), 2.95-3.05(m, 2H), 3.90-4.00(m, 2H), 4.25-4.35(m, 2H), 4.77(s, 2H), 6.60(d, 1H), 6.98(d, 1H), 7.22(m, 1H), 7.39(d, 1H), 8.60(d, 1H) <br> MS APCI+ m/z 368[MH]⁺ | 34% |
| | 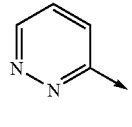 | | |
| 31 | 7-pyridin-2-yl-2-(3-pyrrolidin-1-ylpropoxy)-5,6,7,8-tetrahydro-1,7-naphthyridine | ¹HNMR(CD₃OD, 400 MHz) δ: 1.83(m, 4H), 1.98-2.06(m, 2H), 2.61(m, 4H), 2.68(m, 2H), 2.85(m, 2H), 3.86(m, 2H), 4.32(m, 2H), 4.55(s, 2H), 6.60(d, 1H), 6.66(m, 1H), 6.88(d, 1H), 7.45(d, 1H), 7.58(m, 1H), 8.10(d, 1H) <br> MS APCI+ m/z 399[MH]⁺ | 77% |
| 32 | 7-pyridazin-3-yl-2-(3-pyrrolidin-1-ylpropoxy)-5,6,7,8-tetrahydro-1,7-naphthyridine | ¹HNMR(CD₃OD, 400 MHz)δ: 1.83(m, 4H), 2.02(m, 2H), 2.60(m, 4H), 2.66(m, 2H), 2.89(m, 2H), 3.97(m, 2H), 4.32(m, 2H), 4.69(s, 2H), 6.61(d, 1H), 7.34(m, 1H), 7.42-7.48(m, 2H), 8.48(d, 1H) <br> MS APCI+ m/z 340[MH]⁺ | 74% |

Example 9

Using the 2-bromo-6-(2,2,2-trifluoroethoxy)pyridine of preparation 29.

Example 13

1-Bromo-2,6-naphthyridine precursor can be prepared as described in *Eur. J. Org. Chem* (24), 4181-4184; 2002.

Example 14

Using the 2-chloro-4-ethyl-5-fluoropyridine of preparation 31.

Example 16

2-Chloro-6-ethyl pyridine precursor can be prepared as described in *Heterocycles* 24 (12) 3337-3340; 1986

Example 17

Using the 2-bromo-4-propoxypyridine of preparation 32.

Example 19

6-Bromo-2-(dimethylamino) pyridine precursor can be prepared as described in *J. Org. Chem.* 53 (4), 786-790; 1988.

Example 20

Using the 6-bromo-N,N-dimethylpyridine-2-sulfonamide of preparation 33.

Example 21

3-Chloropyridazine precursor can be prepared as described in *J. Med. Chem.* 30 (2), 239-49; 1987.

Examples 33 to 41

The following compounds of the general formula shown below were prepared from the product of preparations 16 or 17 and the appropriate heterocyclic halide: R¹Cl or R¹Br. A method similar to that described for example 3 was utilised where the reaction mixture was heated in a microwave at 110° C. for 30-60 minutes.

| No. | R¹ | Data | Yield |
|---|---|---|---|

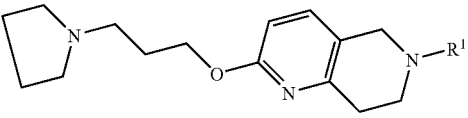

| 33 | 6-pyrimidin-4-yl-2-(3-pyrrolidin-1-ylpropoxy)-5,6,7,8-tetrahydro-1,6-naphthyridine | | |
|---|---|---|---|
| | 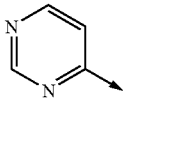 | ¹HNMR(CDCl₃, 400 MHz) δ: 1.73-1.90(brm, 4H), 1.98-2.06(m, 2H), 2.48-2.62(brm, 6H), 2.93-3.02(m, 2H), 3.90-3.98(m, 2H) 4.28-4.35(m, 2H), 4.61-4.65(m, 2H), 6.60(m, 2H), 7.39(m, 1H), 8.21(d, 1H), 8.62(s, 1H)<br>MS APCI+ m/z 340[MH]⁺ | 6% |
| 34 | 6-(6-methylpyridin-2-yl)-2-(3-pyrrolidin-1-ylpropoxy)-5,6,7,8-tetrahydro-1,6-naphthyridine | | |
| | 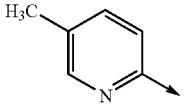 | ¹HNMR(CDCl₃, 400 MHz) δ: 1.70-1.90(brm, 4H), 1.98-2.06(m, 2H), 2.41(s, 3H) 2.50-2.68(brm, 6H), 2.93-3.02(m, 2H), 3.90-3.98(m, 2H) 4.28-4.35(m, 2H), 4.63(s, 2H), 6.50-6.60(m, 3H), 7.37-7.41(m, 2H)<br>MS APCI+ m/z 353[MH]⁺ | 46% |
| 35 | 6-(5-methylpyridin-2-yl)-2-(3-pyrrolidin-1-ylpropoxy)-5,6,7,8-tetrahydro-1,6-naphthyridine | | |
| | 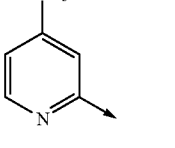 | ¹HNMR(CDCl₃, 400 MHz) δ: 1.70-1.90(m, 4H), 1.98-2.06(m, 2H), 2.20(s, 3H) 2.50-2.68(brm, 6H), 2.93-3.02(m, 2H), 3.80-3.85(m, 2H), 4.28-4.35(m, 2H), 4.59(s, 2H), 6.58(d, 1H), 6.70(d, 1H), 7.37(m, 2H), 8.01(m, 1H)<br>MS APCI+ m/z 353[MH]⁺ | 66% |
| 36 | 6-(4-methylpyridin-2-yl)-2-(3-pyrrolidin-1-ylpropoxy)-5,6,7,8-tetrahydro-1,6-naphthyridine | | |
| | 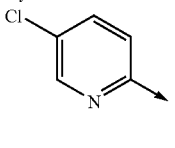 | ¹HNMR(CDCl₃, 400 MHz) δ: 1.70-1.90(m, 4H), 1.98-2.06(m, 2H), 2.23(s, 3H) 2.50-2.68(brm, 6H), 2.93-3.02(m, 2H), 3.84-3.95(m, 2H) 4.28-4.35(m, 2H), 4.59(s, 2H), 6.43(d, 1H), 6.50-6.60(m, 2H), 7.39(d, 1H), 8.05(m, 1H)<br>MS APCI+ m/z 353[MH]⁺ | Quantitative |
| 37 | 6-(5-chloropyridin-2-yl)-2-(3-pyrrolidin-1-ylpropoxy)-5,6,7,8-tetrahydro-1,6-naphthyridine | | |
| | 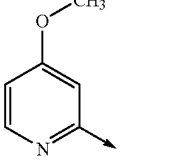 | ¹HNMR(CDCl₃, 400 MHz) δ: 1.90-2.02(m, 4H), 2.13-2.29(m, 2H), 2.35-3.05(brm, 8H), 3.85-3.90(m, 2H), 4.32-4.37(m, 2H), 4.59(s, 2H), 6.57(d, 1H), 6.66(d, 1H), 7.37(d, 1H), 7.45(d, 1H), 8.13(s, 1H)<br>MS APCI+ m/z 373[MH]⁺ | 24% |
| 38 | 6-(4-methoxypyridin-2-yl)-2-(3-pyrrolidin-1-ylpropoxy)-5,6,7,8-tetrahydro-1,6-naphthyridine | | |
| |  | ¹HNMR(CDCl₃, 400 MHz) δ: 1.70-1.90(brm, 4H), 1.98-2.06(m, 2H), 2.50-2.68(brm, 6H), 2.93-3.02(m, 2H), 3.84-3.95(m, 5H), 4.28-4.35(m, 2H), 4.59(s, 2H), 6.19(m, 1H), 6.22(m, 1H), 6.58(d, 1H), 7.39(d, 1H), 8.01(m, 1H)<br>MS APCI+ m/z 369[MH]⁺ | 68% |
| 39 | 6-(3-methoxypyridin-2-yl)-2-(3-pyrrolidin-1-ylpropoxy)-5,6,7,8-tetrahydro-1,6-naphthyridine | | |
| | | ¹HNMR(CDCl₃, 400 MHz) δ: 1.80-1.90(m, 4H), 2.06-2.20(m, 2H), 2.75-2.90(brm, 6H), 3.00(m, 2H), 3.70(m, 2H), 3.82(s, 3H), 4.28-4.35(m, 2H), 4.42(s, 2H), 6.57(d, 1H), 6.81(m, 1H), 7.03(m, 1H), 7.36(d, 1H), 7.92(m, 1H)<br>MS APCI+ m/z 369[MH]⁺ | 35% |

| No. | R¹ | Data | Yield |
|---|---|---|---|
| 40 | 6-(6-morpholin-4-ylpyridin-2-yl)-2-(3-pyrrolidin-2-ylpropoxy)-5,6,7,8-tetrahydro-1,6-naphthyridine | | |
| | 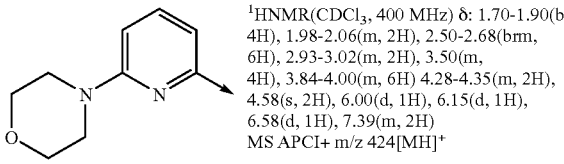 | ¹HNMR(CDCl₃, 400 MHz) δ: 1.70-1.90(brm, 4H), 1.98-2.06(m, 2H), 2.50-2.68(brm, 6H), 2.93-3.02(m, 2H), 3.50(m, 4H), 3.84-4.00(m, 6H) 4.28-4.35(m, 2H), 4.58(s, 2H), 6.00(d, 1H), 6.15(d, 1H), 6.58(d, 1H), 7.39(m, 2H) MS APCI+ m/z 424[MH]⁺ | 51% |

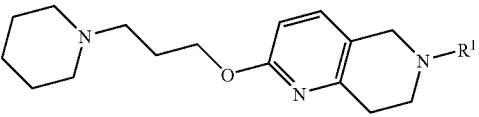

| 41 | 2-(3-piperidin-1-ylpropoxy)-6-pyridin-2-yl-5,6,7,8-tetrahydro-1,6-naphthyridine | | |
|---|---|---|---|
| | 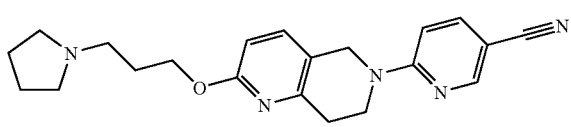 | ¹HNMR(CDCl₃, 400 MHz) δ: 1.42-1.50(m, 2H), 1.60-1.68(m, 4H), 1.95-2.05(m, 2H), 2.45-2.55(m, 6H), 2.90-2.95(m, 2H), 3.93(t, 2H), 4.28(t, 2H), 4.59(s, 2H), 6.61-6.68(m, 2H), 6.91(m, 1H), 7.51(m, 1H), 7.60(m, 1H), 8.11(m, 1H) MS APCI+ m/z 353[MH]⁺ | 36% |

Example 33

4-Chloropyrimidine precursor can be prepared as described in *Bioorg. Chem.*: 30(3), 188-198; 2002.

Example 39

2-Chloro-3-methoxypyridine precursor can be prepared as described in *J. Med. Chem.* 31(3), 618-624; 1988.

Example 40

2-Bromo-5-morpholinopyridine precursor can be prepared as described in *Tet. Lett.* 43 (44), 7967-7969; 2002.

Example 42

6-[2-(3-Pyrrolidin-1-ylpropoxy)-7,8-dihydro-1,6-naphthyridin-6(5H)-yl]nicotinonitrile Potassium carbonate (26.5 mg, 0.19 mmol) was added to a solution of the product of preparation 16 (50 mg, 0.19 mmol) and 4-chlorobenzonitrile (53 mg, 0.38 mmol) in chlorobenzene (2 mL) and the mixture was heated under reflux for 5 hours. The reaction mixture was then partitioned between ethyl acetate and water. The organic layer was separated, dried over magnesium sulfate and concentrated in vacuo to give an orange oil. The oil was purified by column chromatography on silica gel, eluting with ethyl acetate:methanol:0.88 ammonia, 100:0:0 to 80:20:1, to afford the title compound as an orange solid in 55% yield, 38 mg.

¹HNMR(CDCl₃, 400 MHz) δ: 1.70-1.82 (m, 4H), 1.90-2.06 (m, 2H), 2.45-2.70 (brm, 6H), 2.93-3.02 (m, 2H), 3.98 (m, 2H), 4.30 (m, 2H), 4.62 (s, 2H), 6.59 (d, 1H), 6.70 (d, 1H), 7.39 (d, 1H), 7.63 (m, 1H), 8.42 (m, 1H)

MS APCI+ m/z 364 [MH]⁺

Examples 43 to 48

The following compounds of the general formula shown below were prepared from the product of preparations 16, 17 and 20 and the appropriate heterocyclic halide, R¹Cl or R¹Br, using a method similar to that described for example 42. The progress of the reactions was monitored by tlc and the reaction mixture was heated under reflux for 18-48 hours until all of the starting material was consumed.

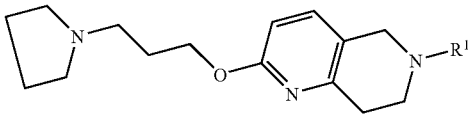

| No. | R¹ | Data | Yield |
|---|---|---|---|
| 43 | 6-[2-(3-pyrrolidin-1-ylpropoxy)-7,8-dihydro-1,6-naphthyridin-6(5H)-yl]nicotinamide  ![H2N-C(=O)-pyridine] | ¹HNMR(CDCl₃, 400 MHz) δ: 1.70-1.90(brm, 4H), 1.95-2.01(m, 2H), 2.42-2.61(brm, 6H), 2.95-3.01(m, 2H), 3.93(m, 2H), 4.30(m, 2H), 4.65(s, 2H), 5.60-5.90(brs, 2H), 6.59(d, 1H), 6.70(d, 1H), 7.39(d, 1H), 7.99(m, 1H) 8.62(m, 1H) MS APCI+ m/z 382[MH]⁺ | 41% |
| 44 | N-methyl-6-[2-(3-pyrrolidin-1-ylpropoxy)-7,8-dihydro-1,6-naphthyridin-6(5H)-yl]nicotinamide | ¹HNMR(CDCl₃, 400 MHz) δ: 1.75-1.81(m, 4H), 2.01-2.05(m, 2H), 2.42-2.61(brm, 6H), 2.95-3.03(m, 5H), 3.93(m, 2H), 4.30(m, 2H), 4.65(s, 2H), 5.95(brs, 1H), 6.59(d, 1H), 6.70(d, 1H), 7.39(d, 1H), 7.97(m, 1H) 8.58(m, 1H) MS APCI+ m/z 396[MH]⁺ | 56% |
| 45 | N,N-dimethyl-6-[2-(3-pyrrolidin-1-ylpropoxy)-7,8-dihydro-1,6-naphthyridin-6(5H)-yl]nicotinamide | ¹HNMR(CDCl₃, 400 MHz) δ: 1.58-1.90(m, 4H), 1.95-2.07(m, 2H), 2.27-2.65(brm, 6H), 2.95-3.03(m, 2H), 3.05-3.15(s, 6H), 3.90-4.00(m, 2H), 4.28-4.37(m, 2H), 4.61-4.70(s, 2H), 6.58(d, 1H), 6.67(d, 1H), 7.37(d, 1H), 7.64-7.70(m, 1H) 8.31-8.38(m, 1H) MS APCI+ m/z 410[MH]⁺ | 39% |
| 46 | N,N-dimethyl-6-[2-(3-pyrrolidin-1-ylpropoxy)-7,8-dihydro-1,6-naphthyridin-6(5H)-yl]pyridine-3-sulfonamide | ¹HNMR(CDCl₃, 400 MHz) δ: 1.76-1.84(m, 4H), 1.99-2.08(m, 2H), 2.45-3.75(brm, 12H), 3.00(m, 2H), 4.00(m, 2H), 4.30(m, 2H), 4.70(s, 2H), 6.60(d, 1H), 6.70(d, 1H), 7.40(d, 1H), 7.80(m, 1H), 8.60(m, 1H) MS APCI+ m/z 446[MH]⁺ | 45% |

[Second scaffold structure with (2R)-2-methylpyrrolidinyl group]

| No. | R¹ | Data | Yield |
|---|---|---|---|
| 47 | 6-[2-{3-[(2R)-2-methylpyrrolidin-1-yl]propoxy}-7,8-dihydro-1,6-naphthyridin-6(5H)-yl]nicotinamide | ¹HNMR(CDCl₃, 400 MHz) δ: 1.11(d, 3H), 1.43(m, 1H), 1.78(m, 2H), 1.91-2.03(m, 3H), 2.16-2.24(m, 2H), 2.38(m, 1H), 2.93(m, 2H), 3.03(m, 1H), 3.19(m, 1H), 4.01(m, 2H), 4.29(m, 2H), 4.69(s, 2H), 6.63(d, 1H), 6.89(d, 1H), 7.51(d, 1H), 8.02(m, 1H), 8.66(d, 1H) MS APCI+ m/z 396[MH]⁺ | 40% |

-continued

| No. | R¹ | Data | Yield |
|---|---|---|---|

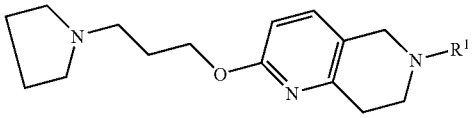

| 48 | 6-[2-(3-piperidin-1-ylpropoxy)-7,8-dihydro-1,6-naphthyridin-6(5H)-yl]nicotinamide | ¹HNMR(CDCl₃, 400 MHz) δ: 1.30-1.80(brm, 6H), 1.91-2.03(m, 2H), 2.30-2.50(m, 6H), 2.95-3.05(m, 2H), 3.95-4.05(m, 2H), 4.27-4.33(m, 2H), 4.72(s, 2H), 6.61(d, 1H), 6.67(d, 1H), 7.39(d, 1H), 7.90-8.20(m, 1H), 8.61(d, 1H) MS APCI+ m/z 396[MH]⁺ | 58% |

Examples 44, 45 and 47 and 48

A few drops of NMP were also added to aid solubility.

Example 45

Using the 6-bromo-N,N-dimethyl-nicotinamide of preparation 36.

Example 46

2-Chloro-5-N,N-dimethylsulfonamidopyridine precursor can be prepared as described in *Helv. Chim. Acta.* 22, 912-920, 1939

Example 49

6-(1,3-Benzoxazol-2-yl)-2-(3-pyrrolidin-1-ylpropoxy)-5,6,7,8-tetrahydro-1,6-naphthyridine

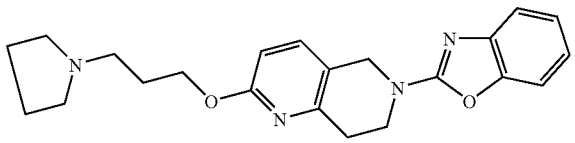

The product of preparation 16 (50 mg, 0.19 mmol), 2-chlorobenzoxazole (29 mg, 0.19 mmol), sodium tert-butoxide, (20 mg, 0.21 mmol), palladium trifluoroacetate (cat.) and tri-ᵗbutylphosphine (cat) were added to toluene (1 mL) and the mixture was heated at 80° C. for 16 hours in a sealed Reactivial® tube. The reaction mixture was then dissolved in ethyl acetate and was purified by column chromatography on silica gel, eluting with ethyl acetate:methanol:0.88 ammonia, 90:10:1, to afford the title compound as a yellow solid in 55% yield, 40 mg.

¹HNMR(CDCl₃, 400 MHz) δ: 1.59-1.90 (brm, 4H), 1.99-2.05 (m, 2H), 2.45-2.65 (brm, 6H), 3.02 (m, 2H), 4.00 (m, 2H), 4.30 (m, 2H), 4.75 (s, 2H), 6.60 (d, 1H), 7.01 (m, 1H), 7.19 (m, 1H), 7.30 (d, 1H), 7.35-7.42 (m, 2H)
MS APCI+ m/z 379 [MH]⁺

Example 50

6-(1-Methyl-1H-benzimidazol-2-yl)-2-(3-pyrrolidin-1-ylpropoxy)-5,6,7,8-tetrahydro-1,6-naphthyridine

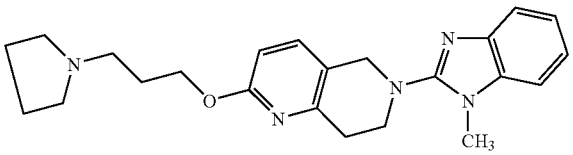

The product of preparation 16 (50 mg, 0.19 mmol), 2-chloro-1-methyl-1H-benzimidazole [(32 mg, 0.19 mmol), *J. Heterocyclic. Chem,* 34(6) 1781-1788; 1997] potassium phosphate, (45 mg, 0.21 mmol), palladium trifluoroacetate (cat.) and tri-ᵗbutylphosphine (cat) were added to xylene (1 mL) and the mixture was heated at 120° C. for 3 hours in a sealed Reactivial® tube. Additional tri-ᵗbutylphosphine (1.8 mg) was added and the mixture was heated for a further 18 hours. The reaction mixture was then dissolved in methanol and was purified by column chromatography on silica gel, eluting with ethyl acetate:methanol:0.88 ammonia, 100:0:0 to 80:20:2. The crude product was purified further by column chromatography on Biotage® amino silica gel, eluting with pentane:ethyl acetate 100:0 to 0:100, to afford the title compound as a colourless oil in 9% yield, 7 mg.

¹HNMR(CDCl₃, 400 MHz) δ: 1.79-1.90 (m, 4H), 1.99-2.05 (m, 2H), 2.50-2.65 (brm, 6H), 3.10 (m, 2H), 3.60 (m, 2H), 3.64 (s, 3H), 4.30 (m, 2H), 4.48 (s, 2H), 6.60 (d, 1H), 7.19 (m, 3H), 7.38 (d, 1H), 7.60 (m, 1H),
MS APCI+ m/z 392 [MH]⁺

Example 51

6-(1,3-Oxazol-2-yl)-2-(3-pyrrolidin-1-ylpropoxy)-5,6,7,8-tetrahydro-1,6-naphthyridine The title compound was prepared from the product of preparation 16 and 2-bromoxazole (*Chem. Mater.* 6 (7), 1023-1032; 1994), using a method similar to example 50, in 2% yield.

$^1$HNMR(CDCl$_3$, 400 MHz) δ: 1.25 (m, 4H), 1,60 (m, 2H), 1.85 (m, 4H), 2.10 (m, 2H), 2.90 (m, 2H), 3.85 (t, 2H), 4.32 (t, 2H), 4.59 (s, 2H), 6.59 (d, 1H), 6.85 (s, 1H), 7.23 (s, 1H), 7.30 (d, 1H)

MS APCI+ m/z 329 [MH]$^+$

Example 52

6-[5-(4-Methoxyphenyl)pyrimidin-2-yl]-2-(3-pyrrolidin-1-yl propoxy)-5,6,7,8-tetrahydro-1,6-naphthyridine

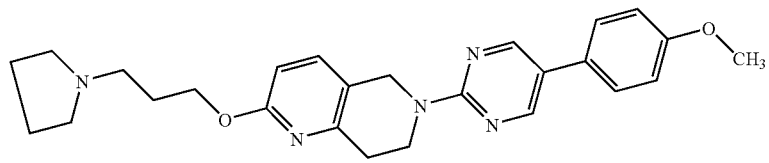

The product of preparation 16 (8 mg, 31 μmol), triethylamine (4.5 μL, 34 μmol), caesium fluoride (9 mg, 0.059 mmol) and 2-chloro-5-(4-methoxyphenyl)pyrimidine [(6.8 mg, 31 μmol), *Bioorg. and Med. Chem. Lett.* 13(4), 761-765; 2003] were mixed in dimethylsulfoxide (300 μL) and heated at 100° C. for 24 hours. The reaction mixture was then cooled and purified by HPLC using a Phenomenex Luna C18 system, eluting with 95:5 to 5:95 acetonitrile: water/acetonitrile/ammonium acetate (95:5:0.005) to afford the title compound.

MS ES+ /m/z 446 [MH]$^+$

Examples 53 to 58

The following compounds of the general formula shown below were prepared from the product of preparation 16 and the appropriate heterocycic halide, R$^2$Cl or R$^2$Br, using a method similar to that described for example 52.

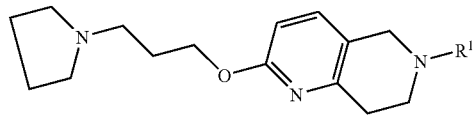

| No. | R$^2$ | MS ES$^+$ m/z |
|---|---|---|
| 53 | 6-[5-(4-methoxyphenoxy)pyrimidin-2-yl]-2-(3-pyrrolidin-1-ylpropoxy)-5,6,7,8-tetrahydro-1,6-naphthyridine 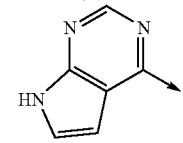 | 462[MH]$^+$ |

-continued

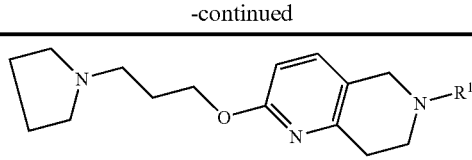

| No. | R$^2$ | MS ES$^+$ m/z |
|---|---|---|
| 54 | 6-(6-methoxypyrimidin-4-yl)-2-(3-pyrrolidin-1-ylpropoxy)-5,6,7,8-tetrahydro-1,6-naphthyridine 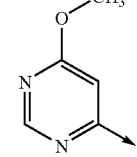 | 370[MH]$^+$ |
| 55 | 6-(9-ethyl-9H-purin-6-yl)-2-(3-pyrrolidin-1-ylpropoxy)-5,6,7,8-tetrahydro-1,6-naphthyridine 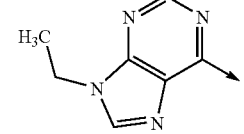 | 408[MH]$^+$ |
| 56 | 2-(3-pyrrolidin-1-ylpropoxy)-6-(7H-pyrrolo[2,3-d]pyrimidin-4-yl)-5,6,7,8-tetrahydro-1,6-naphthyridine 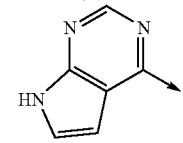 | 379[MH]$^+$ |
| 57 | 6-(9-methyl-9H-purin-6-yl)-2-(3-pyrrolidin-1-ylpropoxy)-5,6,7,8-tetrahydro-1,6-naphthyridine 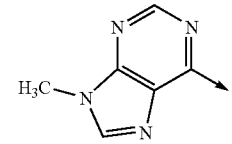 | 394[MH]$^+$ |

-continued

| No. | R² | MS ES⁺ m/z |
|---|---|---|
| 58 | 6-(9H-purin-6-yl)-2-(3-pyrrolidin-1-ylpropoxy)-5,6,7,8-tetrahydro-1,6-naphthyridine 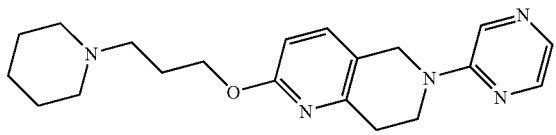 | 380[MH]⁺ |

Example 54

4-Chloro-6-methoxypyrimidineprecursor can be prepared as described in *Helv. Chim. Acta.* 42, 1317-1321; 1959

Example 55

6-Chloro-7-ethylpurine precursor can be prepared as described in *J. Amer. Chem. Soc.* 79, 5 5238-5242; 1957

Example 59

2-(3-Piperidin-1-ylpropoxy)-6-pyrazin-2-yl-5,6,7,8-tetrahydro-1,6-naphthyridine

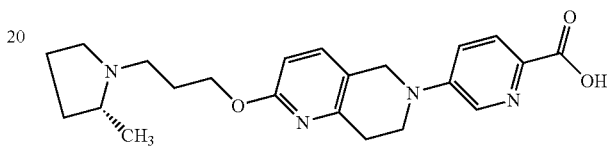

The title compound was prepared from the product of preparation 17 and 2-chloropyrazine, using a similar method to example 3, in 39% yield.

¹HNMR(CDCl₃, 400 MHz) δ: 1.40-1.50 (m, 2H), 1.50-1.70 (brm, 4H), 1.90-2.00 (m, 2H), 2.30-2.50 (brm, 6H), 1.90-2.10 (m, 2H), 3.90-4.00 (m, 2H), 4.25-4.40 (m, 2H), 4.60-4.65 (s, 2H),6.55-6.60 (d, 1H), 7.30-7.40 (d, 1H), 7,86 (m, 1H) 8.05-8.15 (m, 1H), 8.20-8.25 (m, 1H)

MS APCI+ m/z 354 [MH]⁺

Example 60

2-{3-[(2R,5R)-2,5-Dimethylpyrrolidin-1-yl]propoxy}-6-pyridazin-3-yl-5,6,7,8-tetrahydro-1,6-naphthyridine

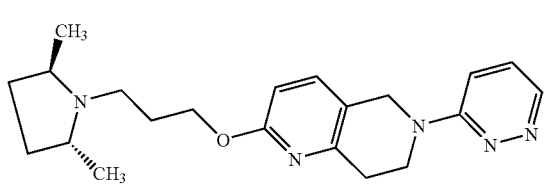

The title compound was prepared from the product of preparation 19 and 2-chloropyridazine, using a similar method to example 3, in 23% yield.

¹HNMR(CDCl₃, 400 MHz) δ: 1.08 (d, 6H), 1.40 (t, 2H), 1.90-2.10 (m, 4H), 2.40-2.55 (m, 1H), 2.70-2.82 (m, 1H), 3.00-3.20 (m, 4H), 3.90-4.00 (m, 2H), 4.20-4.40 (m, 2H), 4.75 (d, 2H), 6.59 (d, 1H), 6.97 (m, 1H), 7.27 (m, 1H), 7.37 (m, 1H), 8.61 (m, 1H)

MS APCI+ m/z 368 [MH]⁺

Example 61

5-[2-{3-[(2R)-2-Methylpyrrolidin-1-yl]propoxy}-7,8-dihydro-1,6-naphthyridin-6(5H)-yl]pyridine-2-carboxylic acid

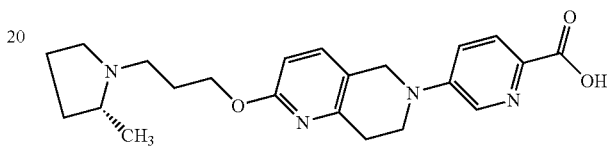

The products of preparation 20 (200 mg, 0.73 mmol) and preparation 34 (188 mg, 0.73 mmol), sodium tert-butoxide, (86 mg, 0.89 mmol), Pd₂(dba)₃ (18 mg, 0.02 mmol) and BINAP (50 mg, 0.08 mmol) were suspended in tert-butanol (5 mL) and the mixture was heated at 110° C. in the microwave for 3 hours. The mixture was replenished with further amounts of sodium tert-butoxide (86 mg, 0.89 mmol), Pd₂(dba)₃ (18 mg, 0.02 mmol) and BINAP (50 mg, 0.08 mmol) at hourly intervals. The reaction mixture was then dissolved in methanol (100 mL) and glacial acetic acid (4 mL) and concentrated to low volume in vacuo. The residue was purified by elution through a SCX-2 ion exchange cartridge, with methanol: 2M ammonia, 100:0 to 80:20. The relevant fractions were concentrated in vacuo and the residue was triturated with diethyl ether to afford the title compound as a pale orange-solid in 84% yield, 285 mg.

¹HNMR(CD₃OD, 400 MHz) δ: 1.33 (d, 3H), 1,65 (m, 1H), 1.94 (m, 2H), 2.05-2.24 (m, 3H), 2.84 (m, 4H), 3.17 (m, 1H), 3.26-3.63 (m, 4H), 4.29 (m, 4H), 6.59 (m, 1H), 7.29 (m, 1H), 7.40 (m, 1H), 7.82 (m, 1H), 8.37 (m, 1H)

MS APCI+ m/z 397 [MH]⁺

Example 62

5-[2-(3-Pyrrolidin-1-ylpropoxy)-7,8-dihydro-1,6-naphthyridin-6(5H)-yl]pyridine-2-carboxylic acid

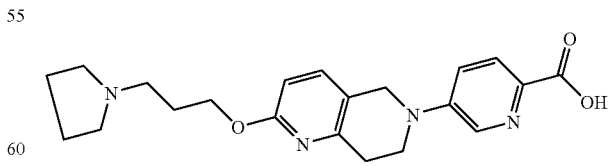

The title compound was prepared from the products of preparation 16 and 34, using a similar method to that of example 61, as an orange solid in 52% yield.

¹HNMR(CD₃OD, 400 MHz) δ: 1.98-2.10 (m, 4H), 2.12-2.24 (m, 2H), 2.75-2.83 (m, 2H), 3.23-3.42 (m, 6H), 3.54-

3.63 (m, 2H), 4.24 (s, 2H), 4.28 (m, 2H), 6.55 (d, 1H), 7.27-7.35 (m, 1H), 7.39 (d, 1H), 7.83 (d, 1H), 8.15-8.19 (m, 1H)

MS APCI+ m/z 383 [MH]+

Example 63

5-[2-[(1-Isopropylpiperidin-4-yl)oxy]-7,8-dihydro-1,6-naphthyridin-6(5H)-yl]pyridine-2-carboxylic acid

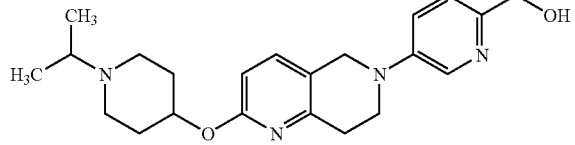

The title compound was prepared from the products of preparation 34 and 39, using a similar method to that of example 61, as an orange solid in 100% yield.

$^1$HNMR(CD$_3$OD, 400 MHz) δ: 1.30 (m, 6H), 2.05 (m, 2H), 2.20 (m, 2H), 2.90 (m, 2H), 3.10 (m, 2H), 3.20-3.45 (brm, 3H), 3.70 (m, 2H), 4.40 (s, 2H), 5.20 (m, 1H), 6.60 (d, 1H), 7.30-7.50 (m, 2H), 7.90 (m, 1H), 8.30 (m, 1H)

MS ES+ m/z 397 [MH]+

Example 64

N-Methyl-5-[2-{3-[(2R)-2-methylpyrrolidin-1-yl]propoxy}-7,8-dihydro-1,6-naphthyridin-6(5H)-yl]pyridine-2-carboxamide

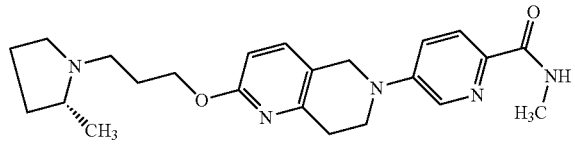

1-Hydroxybenzotriazole hydrate (97 mg, 0.72 mmol), 1-(3-dimethylaminopropyl)-3-ethylcarbodiimide hydrochloride (194 mg, 1.00 mmol), methylamine hydrochloride (234 mg, 3.85 mmol) and N-ethyldiisopropylamine (535 μL, 3.85 mmol) were added to a solution of the product of example 61 (275 mg, 0.69 mmol) in N,N-dimethylacetamide (6 mL) and the mixture was stirred for 72 hours. The reaction mixture was then evaporated under reduced pressure and the residue was suspended in saturated sodium hydrogen carbonate solution. The aqueous mixture was extracted with ethyl acetate (2×40 mL) and the combined extracts were dried over sodium sulfate and concentrated in vacuo. The residue was purified by column chromatography on silica gel, eluting with ethyl acetate:methanol:0.88 ammonia, 100:0:0 to 90:10:1 to give a yellow oil. This oil was further purified by column chromatography on Biotage® amino silica gel, eluting with ethyl acetate:pentane, 0:100 to 100:0 to afford the title compound as a pale yellow solid in 30% yield, 84 mg $^1$HNMR(CD$_3$OD, 400 MHz) δ: 1.13 (d, 3H), 1.42 (m, 1H), 1.77 (m, 2H), 1.92-2.05 (m, 3H), 2.13-2.24 (m, 2H), 2.38 (m, 1H), 2.93 (s, 3H), 2.99 (m, 2H), 3.03 (m, 1H), 3.19 (m, 1H), 3.89 (m, 2H), 4.30 (m, 2H), 4.48 (s, 2H), 6.65 (d, 1H), 7.42 (m, 1H), 7.55 (d, 1H), 7.92 (d, 1H), 8.36 (d, 1H)

MS APCI+ m/z 410 [MH]+

Example 65

N-Methyl-5-[2-(3-pyrrolidin-1-ylpropoxy)-7,8-dihydro-1,6-naphthyridin-6(5H)-yl]pyridine-2-carboxamide

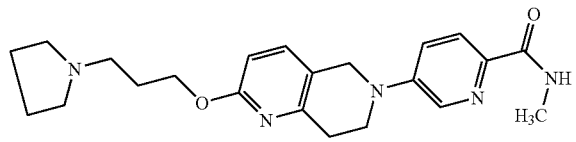

The title compound was prepared from the product of example 62 and methylamine hydrochloride, using a similar method to that of example 64, as a yellow gum in 35% yield.

$^1$HNMR(CDCl$_3$, 400 MHz) δ: 1.75-1.90 (m, 4H), 1.99-2.08 (m, 2H), 2.52-2.70 (m, 6H), 2.98-3.08 (m, 5H), 3.69-3.78 (m, 2H), 4.27-4.37 (m, 2H), 4.42 (s, 2H), 6.60 (d, 1H), 7.20-7.28 (d, 1H), 7.72-7.82 (m, 1H), 8.05-8.10 (d, 1H), 8.18-8.23 (m, 1H)

MS APCI+ m/z 396 [MH]+

Example 66

5-[2-[(1-Isopropylpiperidin-4-yl)oxy]-7,8-dihydro-1,6-naphthyridin-6(5H)-yl]-N-methylpyrididine-2-carboxamide

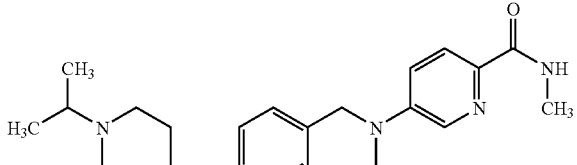

The title compound was prepared from the product of example 63 and methylamine hydrochloride, using a similar method to that of example 64, as a colourless solid in 13% yield.

$^1$HNMR(CD$_3$OD, 400 MHz) δ: 1.05-1.18 (m, 6H), 1.72-1.85 (m, 2H), 2.05 (m, 2H), 2.48 (m, 2H), 2.70-3.00 (brm, 8H), 3.78 (m, 2H), 4.45 (s, 2H), 5.02 (m, 1H), 6.61 (d, 1H), 7.42 (m, 1H), 7.50 (m, 1H), 7.92 (m, 1H), 8.36 (m, 1H)

MS APCI+ m/z 410 [MH]+

Example 67

N,N-Dimethyl-5-[2-(3-pyrrolidin-1-ylpropoxy)-7,8-dihydro-1,6-naphthyridin-6(5H)-yl]pyridine-2-carboxamide

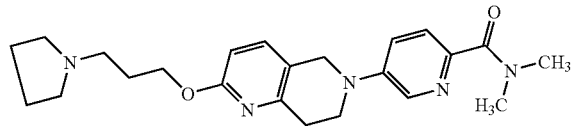

Dimethylamine hydrochloride (50 mg, 0.61 mmol) and O-(1H-benzotriazol-1-yl)-N,N,N',N'-tetramethyluronium hexafluorophosphate (50 mg, 0.16 mmol) were added to a solution of the product of example 62 (45 mg, 0.12 mmol) in N,N-dimethylacetamide (2 mL) and the mixture was stirred for 18 hours. The reaction mixture was then diluted with water and the aqueous mixture was extracted with ethyl acetate (2×). The combined extracts were dried over sodium sulfate and concentrated in vacuo. The residue was purified by column chromatography on silica gel, eluting with ethyl acetate:methanol:0.88 ammonia, 100:0:0 to 90:10:1 to give a yellow oil. This oil was further purified by column chromatography on Biotage® amino silica gel, eluting with ethyl acetate:pentane, 0:100 to 100:0 to afford the title compound as a pale yellow solid in 27% yield, 13 mg $^1$HNMR(CDCl$_3$, 400 MHz) δ: 1.73-1.82 (m, 2H), 1.87-2.05 (m, 4H), 2.45-2.63 (m, 6H), 2.97-3.05 (m, 2H), 3.06 (s, 3H), 3.22 (s, 3H), 3.65-3.72 (m, 2H), 4.28-4.36 (m, 2H), 4.42 (s, 2H), 6.60 (d, 1H), 7.21-7.28 (m, 1H), 7.32-7.38 (m, 1H), 7.61-7.68 (d, 1H), 8.22-8.28 (m, 1H)

MS APCI+ m/z 410 [MH]$^+$

Example 68

N-Methyl-6-[2-{3-[(2R)-2-methylpyrrolidin-1-yl]propoxy}-7,8-dihydro-1,6-naphthyridin-6(5H)-yl]nicotinamide

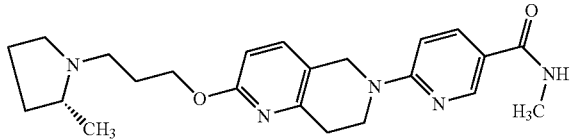

The product of preparation 35 (66 mg, 0.31 mmol), potassium carbonate (38 mg, 0.28 mmol) and NMP (10 μL) were added to a solution of the product of preparation 20 (76 mg, 0.28 mmol) in chlorobenzene (4 mL) and the mixture was heated under reflux for 72 hours. The reaction mixture was then cooled, azeotroped with methanol (30 mL) and evaporated under reduced pressure. The residue was partitioned between ethyl acetate and water and the organic layer was separated, dried over sodium sulfate and concentrated in vacuo. The residue was purified by column chromatography on silica gel, eluting with ethyl acetate:methanol:0.88 ammonia, 100:0:0 to 90:10:1. Re-crystallisation of the relevant fraction from ethyl acetate afforded the title compound as a white solid in 49% yield, 55 mg.

$^1$HNMR(CD$_3$OD, 400 MHz) δ: 1.13 (d, 3H), 1.45 (m, 1H), 1.78 (m, 2H), 1.92-2.06 (m, 3H), 2.17-2.28 (m, 2H), 2.40 (m, 1H), 2.84 (s, 3H), 2.93 (m, 2H), 3.03 (m, 1H), 3.20 (m, 1H), 4.00 (m, 2H), 4.30 (m, 2H), 4.70 (s, 2H), 6.64 (d, 1H), 6.89 (d, 1H), 7.52 (d, 1H), 7.98 (m, 1H), 8.60 (d, 1H)

MS ES+ m/z 410 [MH]$^+$

Example 69

N-Methyl-6-[2-{3-[(2S)-2-methylpyrrolidin-1-yl]propoxy}-7,8-dihydro-1,6-naphthyridin-6(5H)-yl]nicotinamide

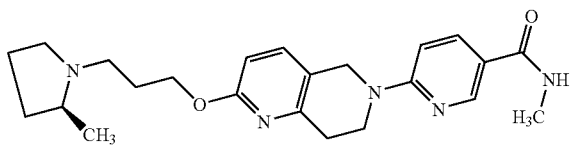

The title compound was prepared for the products of preparations 21 and 35, using a similar method to that of example 68. Purification of the crude product was carried out firstly by column chromatography on silica gel, eluting with ethyl acetate:methanol:0.88 ammonia, 100:0:0 to 90:10:1. Secondly, the resulting oil was purified by column chromatography on Biotage® amino silica gel, eluting with ethyl acetate:pentane, 0:100 to 100:0. Re-crystallisation of the relevant fraction from ethyl acetate then afforded the title compound as a solid in 36% yield.

$^1$HNMR(CD$_3$OD, 400 MHz) δ: 1.13 (d, 3H), 1.45 (m, 1H), 1.78 (m, 2H), 1.92-2.06 (m, 3H), 2.17-2.28 (m, 2H), 2.40 (m, 1H), 2.84 (s, 3H), 2.93 (m, 2H), 3.03 (m, 1H), 3.20 (m, 1H), 4.00 (m, 2H), 4.30 (m, 2H), 4.70 (s, 2H), 6.64 (d, 1H), 6.89 (d, 1H), 7.52 (d, 1H), 7.98 (m, 1H), 8.60 (m, 1H)

MS ES+ m/z 410 [MH]$^+$

Example 70

6-[2-[(1-Isopropylpiperidin4-yl)oxy]-7,8-dihydro-1,6-naphthyridin-6(5H)-yl]-N-methylnicotinamide

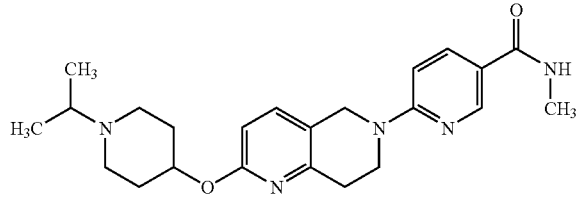

The title compound was prepared from the products of preparations 35 and 39 using a method similar way to example 69, as a white solid in 47% yield.

$^1$HNMR(CD$_3$OD, 400 MHz) δ: 1.09 (m, 6H), 1.80 (m, 2H), 2.05 (m, 2H), 2.47 (m, 2H) 2.77 (m, 1H), 2.85 (m, 2H), 2.89 (s, 3H), 2.94 (m, 2H), 4.00 (m, 2H), 4.68 (s, 2H), 5.03 (m, 1H), 6.61 (d, 1H), 6.89 (d, 1H) 7.50 (d, 1H), 7.98 (m, 1H), 8.61 (m, 1H)

MS ES+ m/z410 [MH]$^+$

Example 71

2-[(1-Isopropylpiperidin-4-yl)oxy]-6-pyrazin-2-yl-5,6,7,8-tetrahydro-1,6-naphthyridine

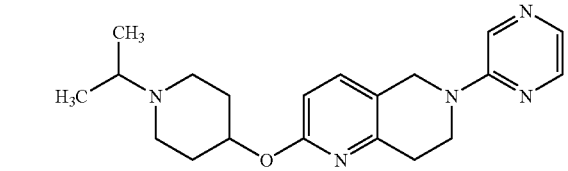

The title compound was prepared from the product of preparation 39 and 2-chloropyrazine, using a method similar to that of example 33, as a yellow oil in 32% yield.

$^1$HNMR(CDCl$_3$, 400 MHz) δ: 0.90-1.18 (m, 6H), 1.70-1.85 (m, 2H), 1.96-2.18 (m, 2H), 2.32-2.56 (m, 2H), 2.67-2.98 (m, 5H), 3.80-3.91 (m, 2H), 4.55 (s, 2H), 5.00 (m, 1H), 6.50 (d, 1H), 7.33 (d, 1H), 7.73-7.87 (m, 1H), 7.99-8.04 (m, 1H), 8.20 (m, 1H)

MS APCI+ m/z 354 [MH]$^+$

Example 72

2-[(1-isoproplpiperidin-4-yl)oxy]-6-(6-methylpyridin-3-yl)-5,6,7,8-tetrahydro-1,6-naphthyridine

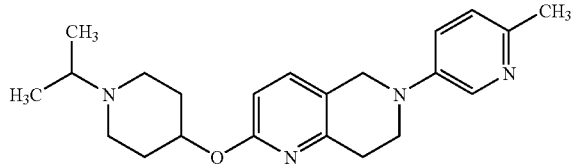

The title compound was prepared from the product of preparation 39 and 5-chloro-2-methylpyridine, using a method similar to that of example 33. Further purification of the crude compound by column chromatography on silica gel, eluting with ethyl acetate:pentane:diethylamine, 65:30:5, afforded the title compound as a yellow oil in 16% yield.

$^1$HNMR(CDCl$_3$, 400 MHz) δ: 0.94-1.08 (m, 6H), 1,63-1.86 (m, 2H), 1.89-2.08 (m, 2H), 2.30-2.40 (m, 5H) 2.64-2.80 (s, 3H), 2.83-3.00 (m, 2H), 3.35-3.63 (m, 2H), 4.18 (s, 2H), 4.79-5.12 (m, 1H), 6.48 (d, 1H), 6.95 (d, 1H) 7.14 (m, 1H), 7.26 (m, 1H), 8.11 (m, 1H)

MS APCI+ m/z 367 [MH]$^+$

Example 73

5-[2-(3-Pyrrolidin-1-ylpropoxy)-7,8-dihydro-1,6-naphthyridin-6(5H)-yl]pyridine-2-carboxamide

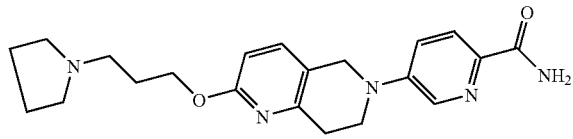

Oxalyl chloride (10 mL) in N,N-dimethylformamide (25 μl) was added to a solution of the product of example 62 (260 mg, 0.34 mmol) in dichloromethane (20 mL) and the mixture was stirred at room temperature for 2 hours. The reaction mixture was then evaporated under reduced pressure and the residue was azeotroped with toluene (10 mL). The residue was then re-dissolved in dichloromethane and a saturated solution of ammonia in dichloromethane (20 mL) was added. The solution was stirred for 2 hours at room temperature. The reaction mixture was then diluted with further dichloromethane (50 mL) and washed with water (20 mL). The aqueous phase was separated and re-extracted with dichloromethane (20 mL) and ethyl acetate (2×20 mL). The combined organic extracts were dried over magnesium sulfate and concentrated in vacuo. Purification of the residue by column chromatography on silica gel, eluting ethyl acetate:methanol: 0.88 ammonia 100:0:0 to 90:10:1 gave the crude product as a brown solid. The solid was triturated with ethyl acetate and purified further by column chromatography on Biotage® amino silica gel, eluting with pentane:ethyl acetate, 100:0 to 0:100 to afford the title compound as a colourless solid in 3% yield, 4 mg.

$^1$HNMR(CD$_3$OD, 400 MHz) δ: 1.83 (m, 4H), 2.02 (m, 2H), 2.60-2.72 (brm, 6H), 2.99 (m, 2H), 3.80 (m, 2H), 4.30 (m, 2H), 4.48 (s, 2H), 6.63 (d, 1H), 7.43 (m, 1H), 7.55 (d, 1H), 7.95 (m, 1H), 8.36 (m, 1H)

MS APCI+ m/z 382 [MH]$^+$

The following Preparations illustrate the synthesis of certain intermediates used in the preparation of the preceding Examples.

Preparation 1: Propiolamide

Methyl propiolate (12.6 g, 150 mmol) was added dropwise to a concentrated ammonium hydroxide solution (42 mL) cooled to −78° C., and the mixture was allowed to stir for 1 hour. The reaction mixture was then warmed to 25° C. over the period of 1 hour and the resulting yellow solution was evaporated under reduced pressure to afford the title compound as a pale yellow solid, 10.5 g.

Preparation 2: 6-Benzyl-5,6,7,8-tetrahydro-1,6-naphthyridin-2(1H)-one

1-Benzyl-4-piperidone (15 g, 79.3 mmol) and pyrrolidine (7.5 mL, 90 mmol) were dissolved in toluene (90 mL) and the solution was heated under reflux, with the removal of water under Dean and Stark conditions, for 5 hours. The solution was then cooled to room temperature and the product of preparation 1 (10.5 g, 150 mmol) was added. The mixture was re-heated under reflux, using Dean and Stark conditions, for a further 8 hours. The reaction mixture was then allowed to cool to room temperature and was triturated with toluene (150 mL) to yield an orange coloured solid. The solid was filtered off and the filtrate was evaporated under reduced pressure to give a red oily residue. The residue was dissolved in dichloromethane (400 mL), washed with saturated sodium hydrogen carbonate solution (2×300 mL), dried over magnesium sulfate and concentrated in vacuo. Purification of the residue by column chromatography on silica gel, eluting with dichloromethane:methanol:0.88 ammonia, 97:3:0.2 to 93:7:0.7, followed by trituration with diethyl ether afforded the title product in 30% yield, 5.57 g.

Preparation 3: 6-Benzyl-2-chloro-5,6,7,8-tetrahydro-1,6-naphthyridine

A mixture of the product of preparation 2 (15.1 g, 63 mmol), phosphorous oxychloride (150 mL) and phosphorous pentachloride (13.2 g, 63 mmol) was heated under reflux for 3 hours. The mixture was then carefully poured onto ice water. The aqueous mixture was neutralised with saturated sodium hydrogen carbonate solution and was extracted with ethyl acetate. The organic phase was dried over sodium sulfate and concentrated in vacuo. The residue was purified by column chromatography on silica gel, eluting with dichloromethane:methanol:0.88 ammonia, 100:0:0 to 95:5:0.5, to afford the title product as a solid in 36% yield, 6 g.

Preparation 4: 3-Pyrrolidin-1-ylpropan-1-ol

3-Bromopropan-1-ol (27.3 mL, 302 mmol) was added to a solution of pyrrolidine (47.2 g, 655 mmol) in toluene (1000 mL) and the mixture was stirred at room temperature for 48 hours. The reaction mixture was then filtered and the filtrate was evaporated under reduced pressure. The residue was distilled and the title product was obtained as a colourless liquid at 100° C./7 mmHg, (23.1 g, 59%).

Preparations 5 to 9

The following compounds of the general formula shown below were prepared from 3-bromopropan-1-ol and the appropriate cyclic amine, using a similar method to preparation 4.

| No. | NR⁷R⁸ | Yield |
|---|---|---|
| 5 | piperidin-1-yl | 52% |
| 6 | azepan-1-yl | 10% |
| 7 | (2S,5S)-2,5-dimethylpyrrolidin-1-yl | 23% |
| 8 | (2S)-2-methylpyrrolidin-1-yl | 39% |
| 9 | (2R)-2-methylpyrrolidin-1-yl | 42% |

Preps 8 and 9: Pure enantiomers of 2-methyl pyrrolidine can be obtained by resolution with +/− tartaric acid as described in *Acta. Pharm. Suecica* 15, 255-263; 1978.

Preps 5-9: Compounds were purified by column chromatography on silica gel, eluting with dichloromethane:methanol: 0.88 ammonia, 100:0:0 to 90:10:1.

Preparation 10: 6-Benzyl-2-(3-pyrrolidin-1-ylpropoxy)-5,6,7,8-tetrahydro-1,6-naphthyridine The product of preparation 4 (1.79 g, 13.9 mmol) was dissolved in tetrahydrofuran (100 mL) and the solution was cooled in an ice bath. 1M Potassium tert-butoxide solution in tetrahydrofuran (23.2 mL, 23.2 mmol) was added dropwise and the solution was stirred at 0° C. for 10 minutes. A solution of the product of preparation 3 (3 g, 11.6 mmol) in tetrahydrofuran (50 mL) was added and the mixture was heated under reflux for 18 hours. The reaction mixture was then cooled to room temperature and was diluted with a mixture of ethyl acetate (150 mL) and brine (150 mL). The layers were separated and the aqueous layer was re-extracted with ethyl acetate (2×150 mL). The organic layers were combined, dried over magnesium sulfate and concentrated in vacuo to give an orange solid. Purification of the solid by column chromatography on silica gel, eluting with dichloromethane:methanol: 0.88 ammonia, 100:0:0 to 95:5:1, afforded the title compound as a colourless solid in 70% yield, 2.67 g.

Preparations 11 to 15

The following compounds of the general formula shown below were prepared from the product of preparation 3 and the appropriate alcohol, using a similar method to preparation 10.

| No. | NR⁷R⁸ | Yield |
|---|---|---|
| 11 | piperidin-1-yl | 98% |
| 12 | azepan-1-yl | 62% |
| 13 | (2S,5S)-2,5-dimethylpyrrolidin-1-yl | 79% |
| 14 | (2S)-2-methylpyrrolidin-1-yl | 50% |
| 15 | (2R)-2-methylpyrrolidin-1-yl | 21% |

Preparation 16: 2-(3-Pyrrolidin-1-ylpropoxy)-5,6,7,8-tetrahydro-1,6-naphthyridine To an ice-cooled solution of the product of preparation 10 (4.55 g, 13.0 mmol) in methanol (250 mL) was added portionwise ammonium formate (4.08 g, 64.8 mmol) and 10% w/w Pd/C (2.5 g). The mixture was heated under reflux for 35 minutes. The reaction mixture was then cooled, diluted with dichloromethane (100 mL) and filtered through Arbocel®, washing through with dichloromethane (200 mL). The filtrate was concentrated in vacuo and the residue was purified by column chromatography on silica gel, eluting with dichloromethane:methanol:0.88 ammonia, 99:1:1 to 80:20:1, to afford the title product as a white solid in 42% yield, 1.43 g Preparations 17 to 21

The following compounds of the general formula shown below were prepared by de-benzylation of the appropriate tetrahydro-1,6-naphthyridine using a method similar to preparation 16.

| No. | NR$^7$R$^8$ | Yield |
|---|---|---|
| 17 | piperidine | 45% |
| 18 | azepane | 68% |
| 19 | (2S,5S)-2,5-dimethylpyrrolidine | 78% |
| 20 | (2S)-2-methylpyrrolidine | 94% |
| 21 | (2R)-2-methylpyrrolidine | 14% |

Preparation 22:
N-(4-Iodopyridin-3-yl)-2,2-dimethylpropanamide

A solution of 2,2-dimethyl-N-pyridin-3-ylpropanamide [(1 g, 5.61 mmol), J. Org. Chem, 48(20), 3401;1998]in tetrahydrofuran (10 mL) and diethyl ether (30 mL) was cooled to −78° C. and TMEDA (2.1 mL, 14 mmol) and "butyl lithium (1.6M in hexane, 8.8 mL, 14 mmol,) were added dropwise. The mixture was stirred for 15 minutes and was then warmed to −10° C. and stirred for a further 2 hours. The reaction mixture was again cooled to −78° C. and a solution of iodine (3.56 g, 14 mmol) in tetrahydrofuran (10 mL) was added dropwise. The resulting slurry was stirred at −78° C. for 2 hours. The mixture was warmed to 0° C. and was quenched with saturated aqueous sodium thiosulfate solution (50 mL). The phases were separated and the aqueous phase was extracted with dichloromethane (2×30 mL). The combined organic phase was dried over magnesium sulfate and concentrated in vacuo. Purification of the residue by column chromatography on silica gel, eluting with pentane:ethyl acetate, 50:50 afforded the title compound as a yellow solid in 38% yield, 655 mg.

Preparation 23: 4-Iodopyridin-3-amine

The product of preparation 22 (4.69 g, 15.4 mmol) and dilute sulphuric acid (24%, 120 mL) were heated under reflux for 1 hour. The mixture was then cooled, basified with solid sodium hydrogen carbonate to pH8 and extracted with dichloromethane (3×200 mL). The combined organic solutions were dried over magnesium sulfate and concentrated in vacuo. Purification of the residue by column chromatography on silica gel, eluting with dichloromethane:methanol, 100:0 to 90:10, afforded the title compound as a brown solid in 90% yield, 3.04 g.

Preparation 24:
Ethyl-3-(3-aminopyridin4-yl)acrylate

The product of preparation 23 (1.1 g, 5 mmol), ethyl acrylate (0.65 mL, 6 mmol), palladium acetate (112 mg, 0.5 mmol), tri-(O-tolyl) phosphine (3.04 mg, 1 mmol), triethylamine (0.84 mL, 6 mmol) and N,N-dimethylformamide (10 mL) were mixed together and heated at 80° C. for 3 hours. The reaction mixture was then cooled to 25° C. and was partitioned between ethyl acetate (20 mL) and water (20 mL). The phases were separated and the aqueous phase was extracted with ethyl acetate (20 mL). The combined organic solutions were washed with brine, dried over magnesium sulfate and concentrated in vacuo. The residue was purified by column chromatography on silica gel, eluting with dichloromethane:methanol, 100:0 to 95:5, to afford the title product as a dark brown oil in 67% yield, 648 mg.

Preparation 25: 1,7-Naphthyridin-2(1H)-one

A solution of the product of preparation 24 (1.32 g, 6.89 mmol) and sodium ethoxide (21% in ethanol, 10.3 mL, 27.56 mmol) in ethanol (30 mL) was heated at 90° C. for 1 hour. The reaction mixture was then cooled to room temperature and was concentrated in vacuo. The residue was purified by column chromatography on silica gel, eluting with dichloromethane:methanol, 100:0 to 90:10, to afford the title compound as a white solid in 63% yield, 635 mg.

Preparation 26: 7-Benzyl-5,6,7,8-tetrahydro-1,7-naphthyridin-2(1H)-one

A suspension of the product of preparation 25 (423 mg, 2.89 mmol) in ethanol (10 mL) was heated at 70° C. for 5 minutes, benzyl bromide (0.34 ml, 2.89 mmol) was then slowly added and the mixture was heated under reflux for 3 hours. The mixture was cooled to 0° C. and sodium borohydride (0.55 g, 14.5 mmol) was added. The mixture was stirred at 0° C. for 10 minutes and was then allowed to warm to room temperature. 6M hydrochloric acid (2 mL) was carefully added and stirring continued at room temperature for 90 minutes. The resulting mixture was basified to pH 10 with 2M sodium hydroxide (10 mL) and was partitioned between ethyl acetate (20 mL) and water (10 mL). The layers were separated and the aqueous was extracted with a dichloromethane/methanol mixture (95:5, 2×20 mL). The organic phases were combined, dried over magnesium sulfate and concentrated in vacuo to afford the title compound as a white solid in 90% yield, 626 mg

Preparation 27: 7-Benzyl-2-(3-pyrrolidin-1-ylpropoxy)-5,6,7,8-tetrahydro-1,7-naphthyridine To a solution of the product of preparation 26 (620 mg, 2.22 mmol) in toluene (30 mL) was added the product of preparation 4 (344 mg, 2.64 mmol), tri-n-butylphosphine (0.66 mL, 2.64 mmol) and 1,1'-azobis(N,N-dimethylformamide) (458 mg, 2.24 mmol) and the reaction mixture was stirred at 85° C. for 18 hours. The solvent was then evaporated under reduced pressure and the residue was purified by column chromatography on silica gel, eluting with dichloromethane:methanol: 0.88 ammonia, 90:10:0.5. The crude product was dissolved in dichloromethane (20 mL), washed with 2M sodium hydroxide, dried over magnesium sulfate and concentrated in vacuo to afford the title compound in 33% yield, 255 mg.

Preparation 28: 2-(3-Pyrrolidin-1-ylpropoxy)-5,6,7,8-tetrahydro-1,7-naphthyridine The title compound was prepared from the product of preparation 27, using a similar method to preparation 16, as a colourless oil in 70% yield.

Preparation 29: 2-Bromo-6-(2,2,2-trifluoroethoxy)pyridine

Sodium hydride (60% dispersion in mineral oil, 0.93 g, 23 mmol) was added to a solution of 2,6-dibromopyridine (5 g, 21 mmol) in N,N-dimethylformamide (10 mL) and the mixture was allowed to stir for 10 minutes. 2,2,2-Trifluoroethanol (2.53 g, 25.2 mmol) was then added and the mixture was heated at 60° C. for 90 minutes. The reaction mixture was then partitioned between water and ethyl acetate and the layers were separated. The organic layer was washed with a further volume of water, dried over magnesium sulfate and concentrated in vacuo to give a liquid residue. Purification of the liquid by column chromatography on silica gel, eluting with petroleum ether (60-80):dichloromethane, 99:1, afforded the title compound as a white liquid in 80% yield, 4.3 g.

Preparation 30: 4-Ethyl-3-fluoropyridine

"Butyllithium (1.6M in tetrahydrofuran, 62.4 ml, 100 mmol) was added dropwise to a solution of diisopropylamine (10 g, 100 mmol) in tetrahydrofuran (110 mL), cooled to −78° C. 3-Fluoropyridine (10 g, 100 mmol) was added dropwise and the reaction mixture was stirred for 1 hour with the temperature maintained below −60° C. Ethyl iodide (31.2 g, 200 mmol) was then added dropwise and the mixture was allowed to stir at room temperature for 30 minutes. The reaction mixture was slowly diluted with water, the solvent was evaporated under reduced pressure and the residue was partitioned between ethyl acetate and water. The organic layer was separated, dried over magnesium sulfate and concentrated in vacuo to give a crude residue. The residue was distilled and title product was obtained during a temperature range of 152-156° C., in 35% yield, 4.46 g.

Preparation 31: 2-Chloro-4-ethyl-5-fluoropyridine

The product of preparation 30 (7.4 g, 50 mmol), aqueous hydrogen peroxide (15%, 15 mL) and acetic acid (25 mL) were mixed together and heated at 60° C. for 24 hours. The reaction mixture was then concentrated in vacuo and azeotroped with water (2×50 mL). The residue was dissolved in dichloromethane (50 mL) and solid sodium carbonate was added until neutralisation occurred. The resulting mixture was stirred for 18 hours at room temperature and was then dried over magnesium sulfate, filtered and concentrated in vacuo to give a yellow oil. The oil was purified by column chromatography on silica gel, eluting with dichloromethane: methanol: 0.88 ammonia, 93:7:1, to afford the intermediate pyridine oxide. The intermediate was then mixed with phosphorus oxychloride (40 mL) and was heated at 120° C. for 30 minutes. The solvent was evaporated under reduced pressure and the residue was dissolved in dichloromethane and poured onto a mixture of ice and 0.88 ammonia. The layers were separated and the organic layer was dried over magnesium sulfate and concentrated in vacuo. The residue was purified by column chromatography on silica gel, eluting with hexane: diethyl ether, 95:5 to afford the title compound as a clear oil in 28% yield, 2.31 g.

Preparation 32: 2-Bromo-4-propoxypyridine

To a solution of sodium (480 mg, 21 mmol) dissolved in 1-propanol (45 mL), was added 2-bromo-4-nitropyridine [(3.2 g, 19.2 mmol), *J. Med. Chem.* 46(7), 1273-1276; 2003] and the mixture was heated at 95° C. for 2 hours. The solvent was then evaporated under reduced pressure and the residue was suspended in chloroform and filtered. The filtrate was washed with water, dried over magnesium sulfate, and concentrated in vacuo to give an oily residue. The residue was distilled and title product was obtained during a temperature range of 145-150° C., as a solid in 58% yield, 2.67 g.

Preparation 33: 6-Bromo-N,N-dimethylpyridine-2-sulfonamide 2,6-Dibromopyridine (12 g, 50 mmol) was dissolved in diethyl ether (150 mL) and the solution was cooled to −70° C. n-Butyl lithium (1.6M in hexane, 35 mL, 55 mmol) was added slowly and the solution was stirred for 15 minutes. Sulfur dioxide gas was then passed through the mixture until a pale yellow precipitate was produced. The reaction mixture was then warmed to room temperature and the solvent was evaporated under reduced pressure. The resulting residue was triturated with petroleum ether to afford the intermediate. The salt was then suspended in dichloromethane, cooled to −70° C. and sulfuryl chloride (75 mL, 93 mmol) was added slowly. The reaction mixture was stirred for 75 minutes and dimethylamine was then added until a basic pH was achieved. The mixture was washed with water and the organic solution was dried over magnesium sulfate and concentrated in vacuo. Trituration of the residue with dichloromethane and petroleum ether afforded the title compound as a white solid in 38% yield, 5.1 g

Preparation 34: 5-Bromo-pyridine-2-carboxylic acid tert-butyl ester para-Toluene sulfonyl chloride (262 mg, 1.38 mmol) was added to a solution of 5-bromo-2-carboxypyridine (118 mg, 0.58 mmol) and pyridine (0.3 mL, 0.39 mmol) in tert-butanol (1 mL) and the mixture was stirred at 40° C. for 10 minutes and room temperature for 2 hours. Saturated sodium hydrogen carbonate solution (4 mL) was then added and the mixture was stirred for 5 minutes. Diethyl ether was next added and the bi-phasic mixture was stirred for a further 10 minutes. The organic layer was then separated, washed with brine, dried over magnesium sulfate and concentrated in vacuo. Purification of the residue by column chromatography on silica gel, eluting with pentane:ethyl acetate, 100:0 to 80:20, afforded the title compound as a colourless solid in 73% yield, 110 mg.

Preparation 35: 6-Bromo-N-methyl-nicotinamide

N,N'-Carbonyldiimidazole (480 mg, 2.96 mmol) was added to a solution of 6-bromonicotinic acid (480 mg, 2.96 mmol) in dimethylsulfoxide (2 mL) and the mixture was stirred for 24 hours. Methylamine (2M in THF, 6 mL, 12 mmol) was then added and the mixture was stirred for a further 18 hours. The reaction mixture was evaporated under reduced pressure and the residue was diluted with water (25 mL) and extracted with dichloromethane (3×10 mL). The combined organic extracts were dried over sodium sulphate and concentrated in vacuo. The residue was purified by column chromatography on silica gel, eluting with ethyl acetate to afford the title compound as a colourless solid in 59% yield, 300 mg.

Preparation 36:
6-Bromo-N,N-dimethyl-nicotinamide

N,N'-Carbonyldiimidazole (1 g, 6.17 mmol) was added to a solution of 6-bromonicotinic acid (1 g, 4.95 mmol) in dimethylsulfoxide (4.16 mL) and the mixture was stirred for 24 hours. Dimethylamine (40% in water, 8.3 mL, 37 mmol) was then added and the mixture was stirred for a further 18 hours. The reaction mixture was then diluted with dichloromethane (20 mL) and washed with water (10 mL). The organic layer was dried over sodium sulphate and concentrated in vacuo. The residue was purified by column chromatography on silica gel, eluting with ethyl acetate to afford the title compound in 46% yield, 520 mg.

Preparation 37: 1-Isopropyl-piperidin-4-ol

A mixture of 4-hydroxypiperidine (10 g, 0.10 mol), acetone (21.8 mL, 0.30 mol), acetic acid (5.7 mL, 0.10 mol) and tetrahydrofuran (150 mL) was stirred in an ice bath for 15 minutes. Sodium triacetoxyborohydride (31.3 g, 0.15mol) was then added portionwise and the mixture was stirred for a further 10 minutes. The reaction mixture was then warmed and stirred at room temperature for 10 minutes and at 40° C. for 2.5 hours. The solvent was evaporated under reduced pressure and the residue was dissolved in water (50 mL). The aqueous solution was basified to pH9 with 0.88 ammonia and the solution was stirred for 30 minutes. The reaction mixture was then extracted with diethyl ether (2×200 mL) and the combined extracts were dried over sodium sulfate and concentrated in vacuo to give a yellow oil. The oil was purified by column chromatography on silica gel, eluting with dichloromethane:methanol:0.88 ammonia, 96:4:1 to 90:10:1, to afford the title product as a yellow oil in quantitative yield, 14.6 g.

Preparation 38: 6-Benzyl-2-[(1-isopropylpiperidin-4-yl)oxy]-5,6,7,8-tetrahydro-1,6-naphthyridine Potassium tert-butoxide (2.37 g, 21 mmol) was added to a solution of the product of preparation 37 (3 g, 21 mmol) in tetrahydrofuran (20 mL) and the solution was stirred at room temperature for 15 minutes. A solution of the product of preparation 3 (1.8 g, 6.9 mmol) in tetrahydrofuran (20 mL) was added and the mixture was heated under reflux for 18 hours. The reaction mixture was then cooled to room temperature and evaporated under reduced pressure. The residue was partitioned between dichloromethane (150 mL) and water (30 mL). The layers were separated and the aqueous layer was re-extracted with dichloromethane (150 mL). The organic layers were combined, dried over sodium sulfate and concentrated in vacuo to give a yellow oil. Purification of the solid by column chromatography on silica gel, eluting with dichloromethane:methanol: 0.88 ammonia, 96:4:1 to 95:5:1, afforded the title compound in 80% yield, 2.02 g.

Preparation 39: 2-[(1-Isopropylpiperidin-4-yl)oxy]-5,6,7,8-tetrahydro-1,6-naphthyridine Palladium (II) hydroxide (50 mg) was added to a solution of the product of preparation 38 (500 mg, 1.37 mmol) and 2M hydrochloric acid (1.37 mL) in ethanol (8 mL) and the mixture was stirred under 50 psi of hydrogen for 2 hours at 50° C. The mixture was then filtered through Arbocel®, washing through with ethanol, and the filtrate was evaporated under reduced pressure. The residue was dissolved in dichloromethane and washed with saturated sodium hydrogen carbonate solution. The organic phase was dried over sodium sulfate and concentrated in vacuo to afford the title product as a colourless oil in 21% yield, 1.43 g A Radioligand Binding Assay for [$^3$H]-dofetilide Binding to the hERG Product Expressed in HEK-293S Cells hERG expressing HEK-293S cells were obtained from University of Wisconsin and membranes prepared according to standard protocols. Membranes were diluted in assay buffer, consisting of Tris-HCl 50 mM; KCl 10 mM; MgCl$_2$ 1 mM pH 7.4 with NaOH, and were pre-coupled with 120 mg/ml YSi polylysine Scintillation Proximity Beads in a ratio of 16 ug protein to 1 mg bead for 2 hours at 4° C. The coupled beads were separated from uncoupled protein by centrifugation and re-suspended in cold assay buffer to give a working solution of 6.25 mgs/ml. 20 µl of test compound was added to a 96-well microtiteplate at a final assay top concentration of 10 µM in serial ½ log dilutions (1 in 3.162) to generate at 10 point IC$_{50}$ curve. 20 µl of $^3$H-UK068798 (Dofetilide, Amersham; specific activity 78-83 Ci/mmole) was placed in each well of a 96 well plate to a final assay concentration of ~5 nM. To this, 160 µl of bead/membrane mixture was added. The assay plates were shaken for 1 hour at room temperature and incubated for a further 30 minutes at room temperature for beads to settle. The plates were then read on a Packard TopCount NXT. The percentage displacement of $^3$H-UK068798 was calculated using 0% as defined by 1% DMSO vehicle in well and 100% as defined by 10 µM UK-068798. Dose response curves were fitted using a four parameter logistical fit and the K$_i$ value was derived using the Cheng-Prusoff equation (Cheng, Y. C. & Prusoff, W. H. (1973). *Biochem. Pharmacol.*, 22, 3099-3108.)

H3 Cell Based Functional Assay

Compounds were evaluated using a cell based functional assay measuring cAMP through β-lactamase reporter gene activity. A stable cell line was generated from HEK-293 cells expressing a CRE β-lactamase reporter gene and transfected with human histamine H$_3$ receptor cDNA. Cells were seeded at a density of 500,000 cells/ml, and grown overnight in MEM (Invitrogen) supplemented with 1% dialysed FBS (Sigma), 2 mM glutamine (Sigma), 1 mM sodium pyruvate (Sigma), 0.1 mM non essential amino acids (Invitrogen) and 25 mM HEPES (Sigma) in poly D lysine coated 384 well plates (BD Biosciences). H₃ receptor agonist imetit (Tocris) dose dependently inhibited 10 μM forskolin (Calbiochem) stimulated synthesis of cAMP measured after 4.5 hours by β-lactamase cleavage of CCF4-AM dye (Invitrogen). For $IC_{50}$ determination, test compounds were prepared in PBS (Sigma) and DMSO (Sigma) at a dose response of $5\times10^{-10}$ to $5\times10^{-5}$ M with a final DMSO concentration in the assay of 0.5%. Cells were incubated for 15 minutes plus/minus compound and their ability to permit 10 μM forskolin-stimulated cAMP synthesis in the presence of 1 nM imetit was measured as described above. Functional $K_i$ values were calculated from the $IC_{50}$ of compounds tested as antagonists based on an experimentally determined imetit $EC_{50}$ (represented in the equation as $K_d$) of 350 pM, and an imetit concentration [L] of 1 nM, according to the Cheng-Prussoff equation where $K_i = (IC_{50})/(1+([L]/K_d))$.

The compounds of the Examples have been tested in the H₃ assays described above and were found to have a $K_i$ value of less than 1000 nM in the H₃ cell based functional assay. The most preferred examples have a $K_i$ value of less than 30 nM in the H₃ cell based functional assay and a $K_i$ value of greater than 4500 nM in the dofetilide binding assay. The data for some of said preferred compounds are given below as a matter of example:

| Ex. No. | $K_i$ (H3 cell based assay - nM) | $K_i$ (dofetilide binding assay - nM) |
| --- | --- | --- |
| 22 | 9.16 | 51750 |
| 23 | 10.28 | 11500 |
| 24 | 8.21 | 35650 |
| 25 | 5.56 | 55900 |
| 26 | 5.24 | 9885 |
| 29 | 19.79 | 64400 |
| 44 | 18.14 | 85800 |
| 48 | 14.54 | 100000 |
| 64 | 4.67 | 55492 |
| 65 | 16.28 | 46057 |
| 67 | 19.65 | 100000 |
| 68 | 8.28 | 100000 |
| 70 | 6.32 | 94353 |
| 71 | 13.73 | 22885 |
| 72 | 4.86 | 13700 |

The invention claimed is:

1. A compound of formula (I):

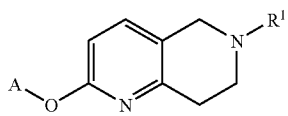

[I]

or formula (I'):

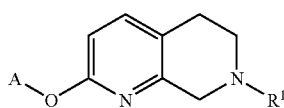

[I']

a stereoisomer thereof, or a pharmaceutically acceptable salt of said compound or stereoisomer, wherein:

$R^1$ is het¹ optionally substituted with one or two halogen; (C₁-C₄)alkyl optionally substituted with halogen; (C₁-C₄)alkoxy optionally substituted with halogen; CN; morpholino; —NR²R³; —(CH₂)ₙC(O)NR²R³; —(CH₂)ₙC(O)O—R⁴; —(CH₂)ₙ—NR⁵—C(O)—R⁴; —(CH₂)ₙ—NR⁵—C(O)—NR²R³; —SO₂—NR²R³; —SO₂(C₁-C₄ alkyl); —R⁶; or —O—R⁶;

n is 0, 1, 2 or 3;

R² and R³ are taken separately and are independently hydrogen or (C₁-C₄)alkyl; or R² and R³ are taken together with the N atom to which they are attached to form a 4-, 5-, 6- or 7-membered saturated heterocycle;

R⁴ and R⁵ are taken separately and are independently hydrogen or (C₁-C₄)alkyl;

R₆ is phenyl optionally substituted with halogen, (C₁-C₄)alkyl or (C₁-C₄)alkoxy;

A is a group of formula:

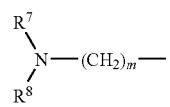

wherein m is 2, 3, 4, 5 or 6; R⁷ and R⁸ are taken separately and are independently hydrogen, (C₁-C₆)alkyl, (C₃-C₇)cycloalkyl or hydroxy(C₁-C₆ alkyl); or R⁷ and R⁸ are taken together with the N atom to which they are attached to form a 4-, 5-, 6- or 7-membered saturated heterocycle wherein one ring —CH₂ group of said heterocycle is optionally replaced by NH, O, S, SO or SO₂ and wherein said saturated heterocycle is optionally and independently substituted with one or two (C₁-C₄)alkyl, (C₁-C₄)alkoxy, (C₁-C₄)alkoxy(C₁-C₄)alkyl, hydroxy(C₁-C₄)alkyl, hydroxy, C(O)O(C₁-C₄)alkyl, —C(O)—(C₁-C₄)alkyl-NH₂, —C(O)NH₂, halo, amino, (C₁-C₄)alkylamino or di[(C₁-C₄)alkyl]amino; or A is a group of formula:

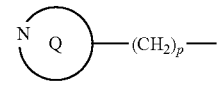

wherein p is 0, 1 or 2; Q is a 4-, 5- or 6-membered saturated heterocycle optionally substituted with hydrogen, (C₁-C₆) alkyl, (C₃-C₇)cycloalkyl, hydroxy(C₁-C₆ alkyl), —(C₁-C₄) alkyl-COOH or —(C₁-C₄)alkyl-O—(C₁-C₄)alkyl-COOH;

het¹ is a monocyclic or bicyclic heteroaromatic group comprising a 5- to 10-membered ring containing 1, 2, 3 or 4 heteroatoms selected from N, O and S.

2. A compound of formula of claim 1, wherein het¹ is a monocyclic heteroaromatic group comprising a 5- or 6-membered ring containing 1 to 2 nitrogen atoms, or 1 nitrogen atom and 1 oxygen atom; or het¹ is a bicyclic aromatic heteroaromatic group comprising a 9- or 10-membered ring containing 1 to 4 nitrogen atoms, or 1 nitrogen atom and 1 oxygen atom.

3. A compound of claim 2, wherein het¹ is a monocyclic heteroaromatic group comprising a 5- or 6-membered ring containing 1 or 2 nitrogen atoms.

4. A compound of claim 3, wherein R¹ is one or two halogen; (C₁-C₄)alkyl optionally substituted with halogen; (C₁-C₄)alkoxy optionally substituted with halogen; CN; morpholino; —NR²R³; —C(O)NR²R³; —SO₂—NR²R³; —R⁶; or —O—R⁶.

5. A compound of claim 4, wherein $R^1$ is $(C_1\text{-}C_4)$alkyl, $(C_1\text{-}C_4)$alkoxy, $C(O)NR^2R^3$ or $-SO_2-NR^2R^3$, and $R^2$ and $R^3$ are taken separately and are independently hydrogen or $(C_1\text{-}C_4)$alkyl.

6. A compound of claim 5 wherein A is a group of formula:

$$\begin{array}{c} R^7 \\ \diagdown \\ N-(CH_2)_m- \\ \diagup \\ R^8 \end{array}$$

wherein m is 2 or 2; $R^7$ and $R^8$ are taken together with the N atom to which they are attached to form a 5- or 6-membered saturated heterocycle optionally substituted with one or two $(C_1\text{-}C_4)$alkyl.

7. A compound of claim 6, wherein $R^7$ and $R^8$ are taken together to form a 5-membered saturated heterocycle optionally substituted with one or two methyl.

8. A compound of claim 5, wherein A is a group of formula:

(N⌒Q)—(CH₂)ₚ— wherein p is 0; and Q is a 6-membered saturated heterocycle optionally substituted on the nitrogen atom with $(C_1\text{-}C_4)$alkyl.

9. A compound having formula (VII) or (XIV):

(VII)

(XIV)

a stereoisomer thereof, or a pharmaceutically acceptable salt of said compound or stereoisomer, wherein:
PG is a protecting group; and
A is a group of formula:

$$\begin{array}{c} R^7 \\ \diagdown \\ N-(CH_2)_m- \\ \diagup \\ R^8 \end{array}$$

wherein m is 2, 3, 4, 5, or 6; $R^7$ and $R^8$ are taken separately and are independently hydrogen, $(C_1\text{-}C_6)$alkyl, $(C_3\text{-}C_7)$cycloalkyl or hydroxy$(C_1\text{-}C_6)$alkyl; or $R^7$ and $R^8$ are taken together with the N atom to which they are attached to form a 4-, 5-, 6- or 7-membered saturated heterocycle, wherein one ring $-CH_2$ group of said heterocycle is optionally replaced by NH, O, S, SO or $SO_2$ and wherein said saturated heterocycle is optionally and independently substituted with one or two $(C_1\text{-}C_4)$alkyl, $(C_1\text{-}C_4)$alkoxy, $(C_1\text{-}C_4)$alkoxy$(C_1\text{-}C_4)$alkyl, hydroxy$(C_1\text{-}C_4$alkyl), hydroxy, $C(O)O(C_1\text{-}C_4)$alkyl, $-C(O)-(C_1\text{-}C_4)$alkyl-$NH_2$, $C(O)NH_2$, halo, amino, $(C_1\text{-}C_4)$alkylamino or di[$(C_1\text{-}C_4)$alkyl]amino; or A is a group of formula:

(N⌒Q)—(CH₂)ₚ— wherein p is 0, 1 or 2; Q is a 4-, 5- or 6-membered saturated heterocycle optionally substituted with hydrogen, $(C_1\text{-}C_6)$alkyl, $(C_3\text{-}C_7)$cycloalkyl, hydroxy$(C_1\text{-}C_6$ alkyl), $-(C_1\text{-}C_4)$alkyl-COOH or $-(C_1\text{-}C_4)$alkyl-O-$(C_1\text{-}C_4)$alkyl-COOH.

10. A compound having formula (VIII) or (XV):

(VIII)

(XV)

a stereoisomer thereof, or a pharmaceutically acceptable salt of said compound or stereoisomer, wherein:
A is a group of formula:

$$\begin{array}{c} R^7 \\ \diagdown \\ N-(CH_2)_m- \\ \diagup \\ R^8 \end{array}$$

wherein m is 2, 3, 4, 5, or 6; $R^7$ and $R^8$ are taken separately and are independently hydrogen, $(C_1\text{-}C_6)$alkyl, $(C_3\text{-}C_7)$cycloalkyl or hydroxy$(C_1\text{-}C_6$ alkyl); or $R^7$ and R8 are taken together with the N atom to which they are attached to form a 4-, 5-, 6- or 7-membered saturated heterocycle, wherein one ring $-CH_2$ group of said heterocycle is optionally replaced by NH, O, S, SO or $SO_2$ and wherein said saturated heterocycle is optionally and independently substituted with one or two $(C_1\text{-}C_4)$alkyl, $(C_1\text{-}C_4)$alkoxy, $(C_1\text{-}C_4)$alkoxy$(C_1\text{-}C_4)$alkyl, hydroxy$(C_1\text{-}C_4$alkyl), hydroxy, $C(O)O(C_1\text{-}C_4)$alkyl, $-C(O)-(C_1\text{-}C_4)$alkyl-$NH_2$, $C(O)NH_2$, halo, amino, $(C_1\text{-}C_4)$alkylamino or di[$(C_1\text{-}C_4)$alkyl]amino; or A is a group of formula:

(N⌒Q)—(CH₂)ₚ— wherein p is 0, 1 or 2; Q is a 4-, 5- or 6-membered saturated heterocycle optionally substituted with hydrogen, $(C_1\text{-}C_6)$alkyl, $(C_3\text{-}C_7)$cycloalkyl, hydroxy$(C_1\text{-}C_6$ alkyl), $-(C_1\text{-}C_4)$alkyl-COOH or $-(C_1\text{-}C_4)$alkyl-O-$(C_1\text{-}C_4)$alkyl-COOH.

11. A pharmaceutical composition comprising a compound of claim 1, a stereoisomer thereof, or a pharmaceutically acceptable salt of said compound or stereoisomer, and pharmaceutically acceptable vehicle, excipient or diluent.

12. A compound selected from:
6-pyrimidin-2-yl-2-(3-pyrrolidin-1-ylpropoxy)-5,6,7,8-tetrahydro-1,6-naphthyridine;

6-pyridin-2-yl-2-(3-pyrrolidin-1-ylpropoxy)-5,6,7,8-tetrahydro-1,6-naphthyridine;
6-pyrazin-2-yl-2-(3-pyrrolidin-1-ylpropoxy)-5,6,7,8-tetrahydro-1,6-naphthyridine;
6-(3-methylpyridin-2-yl)-2-(3-pyrrolidin-1-ylpropoxy)-5,6,7,8-tetrahydro-1,6-naphthyridine;
6-(6-methylpyridin-3-yl)-2-(3-pyrrolidin-1-ylpropoxy)-5,6,7,8-tetrahydro-1,6-naphthyridine;
2-(3-pyrrolidin-1-ylpropoxy)-6-[5-(trifluoromethyl)pyridin-2-yl]-5,6,7,8-tetrahydro-1,6-naphthyridine;
2-(3-pyrrolidin-1-ylpropoxy)-6-[6-(trifluoromethyl)pyridin-2-yl]-5,6,7,8-tetrahydro-1,6-naphthyridine;
2-(3-pyrrolidin-1-ylpropoxy)-6-[4-(trifluoromethyl)pyridin-2-yl]-5,6,7,8-tetrahydro-1,6-naphthyridine;
2-(3-pyrrolidin-1-ylpropoxy)-6-[6-(2,2,2-trifluoroethoxy)pyridin-2-yl]-5,6,7,8-tetrahydro-1,6-naphthyridine;
6-(5-fluoropyridin-2-yl)-2-(3-pyrrolidin-1-ylpropoxy)-5,6,7,8-tetrahydro-1,6-naphthyridine;
6-(6-methoxypyridin-2-yl)-2-(3-pyrrolidin-1-ylpropoxy)-5,6,7,8-tetrahydro-1,6-naphthyridine;
2-(3-pyrrolidin-1-ylpropoxy)-6-quinolin-2-yl-5,6,7,8-tetrahydro-1,6-naphthyridine;
2-[2-(3-pyrrolidin-1-ylpropoxy)-7,8-dihydro-1,6-naphthyridin-6(6h)-yl]-1,5-naphthyridine;
6-(4-ethyl-5-fluoropyridin-2-yl)-2-(3-pyrrolidin-1-ylpropoxy)-5,6,7,8-tetrahydro-1,6-naphthyridine;
6-(4-ethylpyridin-2-yl)-2-(3-pyrrolidin-1-ylpropoxy)-5,6,7,8-tetrahydro-1,6-naphthyridine;
6-(6-ethylpyridin-2-yl)-2-(3-pyrrolidin-1-ylpropoxy)-5,6,7,8-tetrahydro-1,6-naphthyridine;
6-(4-propoxypyridin-2-yl)-2-(3-pyrrolidin-1-ylpropoxy)-5,6,7,8-tetrahydro-1,6-naphthyridine;
6-(3-chloropyridin-2-yl)-2-(3-pyrrolidin-1-ylpropoxy)-5,6,7,8-tetrahydro-1,6-naphthyridine;
N,N-dimethyl-6-[2-(3-pyrrolidin-1-ylpropoxy)-7,8-dihydro-1,6-naphthyridin-6(5h)-yl]pyridine-2-amine;
N,N-dimethyl-6-[2-(3-pyrrolidin-1-ylpropoxy)-7,8-dihydro-1,6-naphthyridin-6(5h)-yl]pyridine-2-sulfonamide;
6-pyridazin-3-yl-2-(3-pyrrolidin-1-ylpropoxy)-5,6,7,8-tetrahydro-1,6-naphthyridine;
2-{3-[(2r)-2-methylpyrrolidin-1-yl]propoxy}-6-pyridazin-3-yl-5,6,7,8-tetrahydro-1,6-naphthyridine;
2-{3-[(2r)-2-methylpyrrolidin-1-yl]propoxy}-6-pyrazin-2-yl-5,6,7,8-tetrahydro-1,6-naphthyridine;
6-(6-methylpyridin-3-yl)-2-{3-[(2r)-2-methylpyrrolidin-1-yl]propoxy}-5,6,7,8-tetrahydro-1,6-naphthyridine;
2-{3-[(2s)-2-methylpyrrolidin-1-yl]propoxy}-6-pyridazin-3-yl-5,6,7,8-tetrahydro-1,6-naphthyridine;
2-{3-[(2s)-2-methylpyrrolidin-1-yl]propoxy}-6-pyrazin-2-yl-5,6,7,8-tetrahydro-1,6-naphthyridine;
6-(6-methylpyridin-3-yl)-2-{3-[(2s)-2-methylpyrrolidin-1-yl]propoxy}-5,6,7,8-tetrahydro-1,6-naphthyridine;
2-{3-[(2r,5r)-2,5-dimethylpyrrolidin-1-yl]propoxy}-6-(6-methylpyridin-3-yl)-5,6,7,8-tetrahydro-1,6-naphthyridine;
2-(3-piperidin-1-ylpropoxy)-6-pyridazin-3-yl-5,6,7,8-tetrahydro-1,6-naphthyridine;
2-(3-azepan-1-ylpropoxy)-6-pyridazin-3-yl-5,6,7,8-tetrahydro-1,6-naphthyridine;
7-pyridin-2-yl-2-(3-pyrrolidin-1-ylpropoxy)-5,6,7,8-tetrahydro-1,6-naphthyridine;
7-pyridazin-3-yl-2-(3-pyrrolidin-1-ylpropoxy)-5,6,7,8-tetrahydro-1,6-naphthyridine;
6-pyrimidin-4-yl-2-(3-pyrrolidin-1-ylpropoxy)-5,6,7,8-tetrahydro-1,6-naphthyridine;
6-(6-methylpyridin-2-yl)-2-(3-pyrrolidin-1-ylpropoxy)-5,6,7,8-tetrahydro-1,6-naphthyridine;
6-(5-methylpyridin-2-yl)-2-(3-pyrrolidin-1-ylpropoxy)-5,6,7,8-tetrahydro-1,6-naphthyridine;
6-(4-methylpyridin-2-yl)-2-(3-pyrrolidin-1-ylpropoxy)-5,6,7,8-tetrahydro-1,6-naphthyridine;
6-(5-chloropyridin-2-yl)-2-(3-pyrrolidin-1-ylpropoxy)-5,6,7,8-tetrahydro-1,6-naphthyridine;
6-(4-methoxypyridin-2-yl)-2-(3-pyrrolidin-1-ylpropoxy)-5,6,7,8-tetrahydro-1,6-naphthyridine;
6-(3-methoxypyridin-2-yl)-2-(3-pyrrolidin-1-ylpropoxy)-5,6,7,8-tetrahydro-1,6-naphthyridine;
6-(6-morpholin-4-ylpyridin-2-yl)-2-(3-pyrrolidin-1-ylpropoxy)-5,6,7,8-tetrahydro-1,6-naphthyridine;
2-(3-piperidin-1-ylpropoxy)-6-pyridin-2-yl-5,6,7,8-tetrahydro-1,6-naphthyridine;
6-[2-(3-pyrrolidin-1-ylpropoxy)-7,8-dihydro-1,6-naphthyridin-6(5h)-yl]nicotinonitrile;
6-[2-(3-pyrrolidin-1-ylpropoxy)-7,8-dihydro-1,6-naphthyridin-6(5h)-yl]nicotinamide;
N-methyl-6-[2-(3-pyrrolidin-1-ylpropoxy)-7,8-dihydro-1,6-naphthyridin-6(5h)-yl]nicotinamide;
N,N-dimethyl-6-[2-(3-pyrrolidin-1-ylpropoxy)-7,8-dihydro-1,6-naphthyridin-6(5h)-yl]nicotinamide;
N,N-dimethyl-6-[2-(3-pyrrolidin-1-ylpropoxy)-7,8-dihydro-1,6-naphthyridin-6(5h)-yl]pyridine-3-sulfonamide;
6-[2-{3-[(2R)-2-methylpyrrolidin-1-yl]propoxy}-7,8-dihydro-1,6-naphthyridin-6(5H)-yl]nicotinamide;
6-[2-(3-piperidin-1-ylpropoxy)-7,8-dihydro-1,6-naphthyridin-6(5h)-yl]nicotinamide;
6-(1,3-benzoxazol-2-yl)-2-(3-pyrrolidin-1-ylpropoxy)-5,6,7,8-tetrahydro-1,6-naphthyridine;
6-(1-methyl-1h-benzimidazol-2-yl)-2-(3-pyrrolidin-1-ylpropoxy)-5,6,7,8-tetrahydro-1,6-naphthyridine;
6-(1,3-oxazol-2-yl)-2-(3-pyrrolidin-1-ylpropoxy)-5,6,7,8-tetrahydro-1,6-naphthyridine;
6-[5-(4-methoxyphenyl)pyrimidin-2-yl]-2-(3-pyrrolidin-1-ylpropoxy)-5,6,7,8-tetrahydro-1,6-naphthyridine;
6-[5-(4-methoxyphenoxy)pyrimidin-2-yl]-2-(3-pyrrolidin-1-ylpropoxy)-5,6,7,8-tetrahydro-1,6-naphthyridine;
6-(6-methoxypyrimidin-4-yl)-2-(3-pyrrolidin-1-ylpropoxy)-5,6,7,8-tetrahydro-1,6-naphthyridine;
6-(9-ethyl-9h-purin-6-yl)-2-(3-pyrrolidin-1-ylpropoxy)-5,6,7,8-tetrahydro-1,6-naphthyridine;
2-(3-pyrrolidin-1-ylpropoxy)-6-(7h-pyrrolo[2,3-d]pyrimidin-4-yl)-5,6,7,8-tetrahydro-1,6-naphthyridine;
6-(9-methyl-9h-purin-6-yl)-2-(3-pyrrolidin-1-ylpropoxy)-5,6,7,8-tetrahydro-1,6-naphthyridine;
6-(9h-purin-6-yl)-2-(3-pyrrolidin-1-ylpropoxy)-5,6,7,8-tetrahydro-1,6-naphthyridine;
2-(3-piperidin-1-ylpropoxy)-6-pyrazin-2-yl-5,6,7,8-tetrahydro-1,6-naphthyridine;
2-{3-[(2r,5r)-2,5-dimethylpyrrolidin-1-yl]propoxy}-6-pyridazin-3-yl-5,6,7,8-tetrahydro-1,6-naphthyridine;
5-[2-{3-[(2r)-2-methylpyrrolidin-1-yl]propoxy}-7,8-dihydro-1,6-naphthyridin-6(5h)-yl]-pyridin-2-carboxylic acid;
5-[2-(3-pyrrolidin-1-ylpropoxy)-7,8-dihydro-1,6-naphthyridin-6(5h)-yl]-pyridin-2-ccarboxylic acid;
5-[2-[(1-isopropylpiperidin-4-yl)oxy]-7,8-dihydro-1,6-naphthyridin-6(5h)-yl]pyridin-2-carboxylic acid;
N-methyl-5-[2-{3-[(2r)-2-methylpyrrolidin-1-yl]propoxy}-7,8-dihydro-1,6-naphthyridin-6(5h)-yl]pyridin-2-carboxamide;

N-methyl-5-[2-(3-pyrrolidin-1-ylpropoxy)-7,8-dihydro-1,6-naphthyridin-6(5h)-yl]pyridin-2-carboxamide;

5-[2-[(1-isopropylpiperidin-4-yl)oxy]-7,8-dihydro-1,6-naphthyridin-6(5h)-yl]-n-methylpyridin-2-carboxamide;

N,N-dimethyl-5-[2-(3-pyrrolidin-1-ylpropoxy)-7,8-dihydro-1,6-naphthyridin-6(5h)-yl]pyridin-2-carboxamide;

N-methyl-6-[2-{3-[(2r)-2-methylpyrrolidin-1-yl]propoxy}-7,8-dihydro-1,6-naphthyridin-6(5h)-yl]nicotinamide;

N-methyl-6-[2-{3-[(2s)-2-methylpyrrolidin-1-yl]propoxy}-7,8-dihydro-1,6-naphthyridin-6(5h)-yl]nicotinamide;

6-[2-[(1-isopropylpiperidin-4-yl)oxy]-7,8-dihydro-1,6-naphthyridin-6(5h)-yl]-n-methylnicotinamide;

2-[(1-isopropylpiperidin-4-yl)oxy]-6-pyrazin-2-yl-5,6,7,8-tetrahydro-1,6-naphthyridine;

2-[(1-isopropylpiperidin-4-yl)oxy]-6-(6-methylpyridin-3-yl)-5,6,7,8-tetrahydro-1,6-naphthyridine; or 5-[2-(3-pyrrolidin-1-ylpropoxy)-7,8-dihydro-1,6-naphthyridin-6(5h)-yl]pyridin-2-carboxamide;

or a stereoisomer thereof, or a pharmaceutically acceptable salt of said compound or stereoisomer.

13. A compound of claim 12 selected from:

7-pyridazin-3-yl-2-(3-pyrrolidin-1-ylpropoxy)-5,6,7,8-tetrahydro-1,7-naphthyridine;

6-pyrazin-2-yl-2-(3-pyrrolidin-1-ylpropoxy)-5,6,7,8-tetrahydro-1,6-naphthyridine;

6-(6-methylpyridin-3-yl)-2-(3-pyrrolidin-1-ylpropoxy)-5,6,7,8-tetrahydro-1,6-naphthyridine;

6-pyridazin-3-yl-2-(3-pyrrolidin-1-ylpropoxy)-5,6,7,8-tetrahydro-1,6-naphthyridine;

N-methyl-6-[2-(3-pyrrolidin-1-ylpropoxy)-7,8-dihydro-1,6-naphthyridin-6(5h)-yl]nicotinamide;

6-[2-(3-piperidin-1-ylpropoxy)-7,8-dihydro-1,6-naphthyridin-6(5h)-yl]nicotinamide 2-(3-piperidin-1-ylpropoxy)-6-pyridazin-3-yl-5,6,7,8-tetrahydro-1,6-naphthyridine;

N,N-dimethyl-6-[2-(3-pyrrolidin-1-ylpropoxy)-7,8-dihydro-1,6-naphthyridin-6(5h)-yl]nicotinamide;

2-{3-[(2r)-2-methylpyrrolidin-1-yl]propoxy}-6-pyridazin-3-yl-5,6,7,8-tetrahydro-1,6-naphthyridine;

6-(6-methylpyridin-3-yl)-2-{3-[(2r)-2-methylpyrrolidin-1-yl]propoxy}-5,6,7,8-tetrahydro-1,6-naphthyridine;

2-{3-[(2r)-2-methylpyrrolidin-1-yl]propoxy}-6-pyrazin-2-yl-5,6,7,8-tetrahydro-1,6-naphthyridine;

N-methyl-5-[2-(3-pyrrolidin-1-ylpropoxy)-7,8-dihydro-1,6-naphthyridin-6(5h)-yl]pyridin-2-carboxamide;

2-{3-[(2s)-2-methylpyrrolidin-1-yl]propoxy}-6-pyridazin-3-yl-5,6,7,8-tetrahydro-1,6-naphthyridine;

2-{3-[(2s)-2-methylpyrrolidin-1-yl]propoxy}-6-pyrazin-2-yl-5,6,7,8-tetrahydro-1,6-naphthyridine;

6-(6-methylpyridin-3-yl)-2-{3-[(2s)-2-methylpyrrolidin-1-yl]propoxy}-5,6,7,8-tetrahydro-1,6-naphthyridine;

N-methyl-6-[2-{3-[(2r)-2-methylpyrrolidin-1-yl]propoxy}-7,8-dihydro-1,6-naphthyridin-6(5h)-yl]nicotinamide;

2-[(1-isopropylpiperidin-4-yl)oxy]-6-pyrazin-2-yl-5,6,7,8-tetrahydro-1,6-naphthyridine;

N,N-dimethyl-5-[2-(3-pyrrolidin-1-ylpropoxy)-7,8-dihydro-1,6-naphthyridin-6(5h)-yl]pyridin-2-carboxamide;

N-methyl-5-[2-{3-[(2r)-2-methylpyrrolidin-1-yl]propoxy}-7,8-dihydro-1,6-naphthyridin-6(5h)-yl]pyridin-2-carboxamide;

N-methyl-6-[2-{3-[(2s)-2-methylpyrrolidin-1-yl]propoxy}-7,8-dihydro-1,6-naphthyridin-6(5h)-yl]nicotinamide;

2-[(1-isopropylpiperidin-4-yl)oxy]-6-(6-methylpyridin-3-yl)-5,6,7,8-tetrahydro-1,6-naphthyridine;

6-[2-[(1-isopropylpiperidin-4-yl)oxy]-7,8-dihydro-1,6-naphthyridin-6(5h)-yl]-n-methylnicotinamide;

5-[2-[(1-isopropylpiperidin-4-yl)oxy]-7,8-dihydro-1,6-naphthyridin-6(5h)-yl]pyridin-2-carboxamide; or 5-[2-(3-pyrrolidin-1-ylpropoxy)-7,8-dihydro-1,6-naphthyridin-6(5h)-yl]pyridin-2-carboxamide, or a stereoisomer thereof, or a pharmaceutically acceptable salt of said compound or stereoisomer.

14. A compound of claim 13 selected from 6-[2-[(1-Isopropylpiperidin-4-yl)oxy]-7,8-dihydro-1,6-naphthyridin-6(5H)-yl]-N-methylnicotinamide, a stereoisomer thereof, or a pharmaceutically acceptable salt of said compound or stereoisomer.

* * * * *